US010208023B2

(12) United States Patent
Pajouhesh et al.

(10) Patent No.: US 10,208,023 B2
(45) Date of Patent: *Feb. 19, 2019

(54) HETEROCYCLIC INHIBITORS OF THE SODIUM CHANNEL

(71) Applicant: Mark G. DeGiacomo, Boston, MA (US)

(72) Inventors: Hassan Pajouhesh, West Vancouver (CA); Richard Holland, Vancouver (CA); Lingyun Zhang, Vancouver (CA); Hossein Pajouhesh, Coquitlam (CA); Jason Lamontagne, Burnaby (CA); Brendan Whelan, Vancouver (CA)

(73) Assignee: Mark G. DeGiacomo, Boston, MA (US), interim trustee ( * ) Notice: Subject to any disclaimer, the term of this patent is extended or adjusted under 35 U.S.C. 154(b) by 0 days.

This patent is subject to a terminal disclaimer.

(21) Appl. No.: 14/771,628

(22) PCT Filed: Feb. 27, 2014

(86) PCT No.: PCT/US2014/019026
§ 371 (c)(1),
(2) Date: Aug. 31, 2015

(87) PCT Pub. No.: WO2014/134306
PCT Pub. Date: Sep. 4, 2014

(65) Prior Publication Data
US 2016/0016939 A1 Jan. 21, 2016

Related U.S. Application Data

(60) Provisional application No. 61/771,360, filed on Mar. 1, 2013.

(51) Int. Cl.

| | | |
|---|---|---|
| *C07D 403/06* | (2006.01) | |
| *C07D 403/04* | (2006.01) | |
| *C07D 403/12* | (2006.01) | |
| *C07D 233/76* | (2006.01) | |
| *C07D 401/04* | (2006.01) | |
| *C07D 235/14* | (2006.01) | |
| *C07D 401/12* | (2006.01) | |
| *C07D 241/08* | (2006.01) | |
| *C07D 241/44* | (2006.01) | |
| *C07D 265/30* | (2006.01) | |
| *C07D 207/08* | (2006.01) | |
| *C07D 207/16* | (2006.01) | |
| *C07D 211/58* | (2006.01) | |

(Continued)

(52) U.S. Cl.
CPC .......... *C07D 403/06* (2013.01); *C07C 237/08* (2013.01); *C07C 237/18* (2013.01); *C07C 237/20* (2013.01); *C07C 237/24* (2013.01); *C07D 207/08* (2013.01); *C07D 207/09* (2013.01); *C07D 207/16* (2013.01); *C07D 211/58* (2013.01); *C07D 211/60* (2013.01); *C07D 233/76* (2013.01); *C07D 235/14* (2013.01); *C07D 241/08* (2013.01); *C07D 241/44* (2013.01); *C07D 265/30* (2013.01); *C07D 295/18* (2013.01); *C07D 295/185* (2013.01); *C07D 401/04* (2013.01); *C07D 401/12* (2013.01); *C07D 403/04* (2013.01); *C07D 403/12* (2013.01)

(58) Field of Classification Search
CPC .. C07D 403/06; C07D 403/12; C07D 403/04; C07D 207/08; C07D 207/09; C07D 207/16; C07D 295/18; C07D 295/185; C07D 235/14; C07D 233/76; C07D 211/58; C07D 211/60; C07D 241/08; C07D 241/44; C07D 401/04; C07D 401/12; C07D 265/30; C07C 237/08; C07C 237/18; C07C 237/20; C07C 237/24

See application file for complete search history.

(56) References Cited

U.S. PATENT DOCUMENTS

| | | |
|---|---|---|
| 5,198,449 A | 3/1993 | Shanklin, Jr. |
| 5,559,127 A | 9/1996 | Hartman et al. |

(Continued)

FOREIGN PATENT DOCUMENTS

| | | |
|---|---|---|
| CA | 2022451 A1 | 2/1991 |
| CA | 2198084 A1 | 2/1996 |

(Continued)

OTHER PUBLICATIONS

Chemical Abstracts Registry No. 59052-85-6, indexed in the Registry file on STN CAS Online on Nov. 16, 1984.*

(Continued)

*Primary Examiner* — Clinton A Brooks
(74) *Attorney, Agent, or Firm* — Entralta P.C.; Jeffrey M. McQuiston; Peter D. Weinstein

(57) ABSTRACT

The invention relates to compounds useful in treating conditions associated with voltage-gated ion channel function, particularly conditions associated with sodium channel activity. More specifically, the invention concerns heterocyclic compounds (e.g., compounds according to any of Formulas (I)-(X) or Compounds (1)-(92) of Table 1) that are that are useful in treatment of conditions such as epilepsy, cancer, pain, migraine, Parkinson's Disease, mood disorders, schizophrenia, psychosis, tinnitus, amyotrophic lateral sclerosis, glaucoma, ischemia, spasticity disorders, obsessive compulsive disorder, restless leg syndrome and Tourette syndrome.

15 Claims, No Drawings

(51) Int. Cl.
*C07D 211/60* (2006.01)
*C07D 295/18* (2006.01)
*C07C 237/08* (2006.01)
*C07C 237/18* (2006.01)
*C07C 237/20* (2006.01)
*C07C 237/24* (2006.01)
*C07D 207/09* (2006.01)
*C07D 295/185* (2006.01)

(56) References Cited

U.S. PATENT DOCUMENTS

| | | | |
|---|---|---|---|
| 5,852,014 | A | 12/1998 | Gaster et al. |
| 5,932,737 | A * | 8/1999 | Itoh .................. C07K 5/06043 546/256 |
| 6,011,035 | A | 1/2000 | Snutch et al. |
| 6,294,533 | B1 | 9/2001 | Snutch et al. |
| 6,387,897 | B1 | 5/2002 | Snutch |
| 6,531,612 | B2 | 3/2003 | Gabriel et al. |
| 6,544,997 | B1 | 4/2003 | Bosmans et al. |
| 6,617,322 | B2 | 9/2003 | Snutch |
| 6,951,862 | B2 | 10/2005 | Snutch et al. |
| 6,984,637 | B2 | 1/2006 | Gong et al. |
| 7,067,665 | B2 | 6/2006 | Nazare et al. |
| 7,244,758 | B2 | 7/2007 | Pajouhesh et al. |
| 7,259,157 | B2 | 8/2007 | Liverton et al. |
| 7,507,760 | B2 | 3/2009 | Pajouhesh et al. |
| 8,377,968 | B2 | 2/2013 | Pajouhesh et al. |
| 8,841,483 | B2 | 9/2014 | Joshi et al. |
| 2003/0013721 | A1 | 1/2003 | Meghani et al. |
| 2003/0086980 | A1 | 5/2003 | Shin et al. |
| 2003/0087799 | A1 | 5/2003 | Wolfart et al. |
| 2003/0125269 | A1 | 7/2003 | Li |
| 2004/0044004 | A1 | 3/2004 | Snutch et al. |
| 2004/0197825 | A1 | 10/2004 | Karicheti et al. |
| 2004/0259866 | A1 | 12/2004 | Snutch et al. |
| 2004/0266784 | A1 | 12/2004 | Snutch et al. |
| 2006/0003985 | A1 | 1/2006 | Renger et al. |
| 2006/0025397 | A1 | 2/2006 | Shin et al. |
| 2006/0025438 | A1* | 2/2006 | Salter-Cid ............ A61K 31/135 514/303 |
| 2006/0084660 | A1 | 4/2006 | Snutch et al. |
| 2009/0029883 | A1 | 1/2009 | Loh et al. |
| 2009/0105251 | A1 | 4/2009 | Jones et al. |
| 2009/0298834 | A1 | 12/2009 | Pajouhesh et al. |
| 2011/0052562 | A1 | 3/2011 | Feng et al. |
| 2011/0212973 | A1 | 9/2011 | Ishii et al. |
| 2011/0224255 | A1 | 9/2011 | Breslin et al. |
| 2012/0028937 | A1 | 2/2012 | Tsuzuki et al. |
| 2012/0184533 | A1 | 7/2012 | Panicker et al. |
| 2014/0187533 | A1 | 7/2014 | Pajouhesh et al. |
| 2015/0361032 | A1 | 12/2015 | Pajouhesh et al. |
| 2017/0107203 | A1* | 4/2017 | Pajouhesh ............ C07D 403/12 |

FOREIGN PATENT DOCUMENTS

| | | |
|---|---|---|
| CA | 2286870 A1 | 10/1998 |
| CA | 2318601 A1 | 8/1999 |
| CA | 2345210 A1 | 5/2000 |
| CA | 2497827 A1 | 3/2004 |
| CA | 2605603 A1 | 11/2006 |
| CA | 2659512 A1 | 12/2007 |
| CA | 2665736 A1 | 5/2008 |
| CA | 2695496 A1 | 2/2009 |
| CA | 2703106 A1 | 4/2009 |
| CA | 2711977 A1 | 7/2009 |
| CA | 2828456 A1 | 9/2012 |
| CA | 2861439 A1 | 8/2013 |
| CN | 1252798 A | 5/2000 |
| EP | 1343780 B1 | 9/2006 |
| FR | 2769914 A1 | 4/1999 |
| GB | 1434323 A | 5/1976 |
| GR | 1003885 B | 5/2002 |
| JP | 2001-518906 A | 10/2001 |
| JP | 2006-143667 A | 6/2006 |
| WO | WO-98/46589 A2 | 10/1998 |
| WO | WO-01/10799 A1 | 2/2001 |
| WO | WO-01/21615 A1 | 3/2001 |
| WO | WO-02/50061 A1 | 6/2002 |
| WO | 2002088138 A1 | 11/2002 |
| WO | WO-03/007953 A1 | 1/2003 |
| WO | WO-2004/000311 A2 | 12/2003 |
| WO | 2004022060 A2 | 3/2004 |
| WO | WO-2004/046110 A1 | 6/2004 |
| WO | WO-2004/063180 A1 | 7/2004 |
| WO | WO-2005/077082 A2 | 8/2005 |
| WO | WO-2005/086971 A2 | 9/2005 |
| WO | WO-2005/092882 A1 | 10/2005 |
| WO | WO-2007/002361 A2 | 1/2007 |
| WO | WO-2007/002884 A2 | 1/2007 |
| WO | WO-2007/053819 A2 | 5/2007 |
| WO | WO-2007/056155 A1 | 5/2007 |
| WO | WO-2007/077508 A2 | 7/2007 |
| WO | WO-2007/078990 A2 | 7/2007 |
| WO | WO-2007/118323 A1 | 10/2007 |
| WO | WO-2008/031227 A1 | 3/2008 |
| WO | WO-2008/109175 A1 | 9/2008 |
| WO | WO-2008/157844 A1 | 12/2008 |
| WO | WO-2009/064388 A2 | 5/2009 |
| WO | WO-2009/136625 A1 | 11/2009 |
| WO | WO-2009/146540 A1 | 12/2009 |
| WO | WO-2010/023196 A2 | 3/2010 |
| WO | WO-2010/023197 A2 | 3/2010 |
| WO | WO-2010/053120 A1 | 5/2010 |
| WO | WO-2010/080357 A1 | 7/2010 |
| WO | WO-2010/087399 A1 | 8/2010 |
| WO | WO-2010/102663 A1 | 9/2010 |
| WO | WO-2011/032291 A1 | 3/2011 |
| WO | WO-2012/116440 A1 | 9/2012 |
| WO | WO-2013/131018 A1 | 9/2013 |
| WO | 2014134306 A1 | 9/2014 |
| WO | WO-2015/127549 A1 | 9/2015 |
| WO | WO-2015/130957 A1 | 9/2015 |

OTHER PUBLICATIONS

Bee et al, Neuropharmacology, 57(2009), 472-479.*
Arimoto et al., "Semisynthetic beta-lactam antibiotics. III. Synthesis and antibacterial activity of 7 beta-[2-(2-aminothiazol-4-yl)-2-(substituted carbamoylmethoxyimino)acetamido]cephalosporins," J Antibiot (Tokyo). 39(9):1243-56 (1986).
Astles et al., "Diamine containing VLA-4 antagonists," Bioorg Med Chem. 9(8):2195-202 (2001).
Augustine et al., "Calcium action in synaptic transmitter release," Annu Rev Neurosci. 10:633-93 (1987).
Banker et al., *Modern Pharmaceutics, 3rd Edition.* Marcel Dekker, Inc., 451 and 596 (1996).
Barton et al., "The antihyperalgesic effects of the T-type calcium channel blockers ethosuximide, trimethadione, and mibefradil," Eur J Pharmacol. 521(1-3):79-85 (2005).
Bavetsias et al., "Imidazo[4,5-b]pyridine derivatives as inhibitors of Aurora kinases: lead optimization studies toward the identification of an orally bioavailable preclinical development candidate," J Med Chem. 53(14):5213-28 (2010).
Caplus Accession for JP 2006143667, dated Jun. 8, 2006 (2 pages).
Caplus Accession for WO 2002/022592, dated Mar. 21, 2002 (4 pages).
Caplus Accession for Young et al., "Pyrrolidine-carboxamides and oxadiazoles as potent hNK1 antagonists," Bioorganic & Medicinal Chemistry Letters 17(19):5310-5315, 2007 (1 page).
CAS Registry No. 1027575-54-7. Entered on Jun. 12, 2008 (1 page).
Catterall, "Structure and regulation of voltage-gated $Ca^{2+}$ channels," Annu Rev Cell Dev Biol. 16:521-55 (2000).
Chinese Office Action issued for Chinese Application No. 2010/80050517.1, dated Dec. 2, 2013 (11 pages).
Coenen, "Genetic animal models for absence epilepsy: a review of the WAG/Rij strain of rats," Behav Genet. 33(6):635-655 (2003).
Diouf et al., "Synthesis and preliminary pharmacological results on new naphthalene derivatives as 5-HT(4) receptor ligands," Eur J Med Chem. 35(7-8):699-706 (2000).

(56) References Cited

OTHER PUBLICATIONS

Dogrul et al., "Reversal of experimental neuropathic pain by T-type calcium channel blockers," Pain. 105(1-2):159-68 (2003).
Dörwald, *Side Reactions in Organic Synthesis: A Guide to Successful Synthesis Design*, WILEY-VCH Verlag GmbH & Co. KGaA, 1-16, 40-1, 278-309 (2005) (37 pages).
English translation of Examination Report for Israeli Patent Application No. 218143, dated Sep. 8, 2013 (2 pages).
Examination Report for New Zealand Patent Application No. 598304, dated Oct. 30, 2012 (2 pages).
Extended European Search Report for European Application No. 09757002.2, dated Nov. 24, 2011 (6 pages).
Extended European Search Report for European Application No. 10813213.5, dated Jun. 17, 2013 (7 pages).
Gataullin et al., "Synthesis and local anesthetic activity of 3,4-difluoroaniline derivatives," Pharmaceutical Chemistry Journal 33(5):255-8 (1999).
Gomora et al., "Block of cloned human T-type calcium channels by succinimide antiepileptic drugs," Mol Pharmacol. 60(5):1121-32 (2001).
Hayashi et al., "Pathophysiological significance of T-type Ca2+ channels: role of T-type Ca2+ channels in renal microcirculation," J Pharmacol Sci. 99(3):221-7 (2005).
Heady et al., "Molecular pharmacology of T-type Ca2+ channels," Jpn J Pharmacol. 85(4):339-50 (2001).
Heo et al., "T-type Ca2+ channel blockers suppress the growth of human cancer cells," Bioorg Med Chem Lett. 18(14):3899-901 (2008).
Huguenard, "Low-threshold calcium currents in central nervous system neurons," Annu Rev Physiol. 58:329-48 (1996).
Hulme et al., "Applications of N-BOC-diamines for the solution phase synthesis of ketopiperazine libraries utilizing a Ugi/De-BOC/Cyclization (UDC) strategy," Tetrahedron Letters 39:8047-50 (1998).
Hulme et al., "Novel applications of ethyl glyoxalate with the Ugi MCR," Tetrahedron Letters 40:5295-9 (1999).
Hulme et al., "Novel applications of resin bound alpha-amino acids for the synthesis of benzodiazepines (via Wang resin) and ketopiperazines (via hydroxymethyl resin)," Tetrahedron Letters 41:1509-14 (2000).
Hulme et al., "Novel safety-catch linker and its application with a Ugi/De-BOC/Cyclization (UDC) strategy to access carboxylic acids, 1,4-benzodiazepines, diketopiperazines, ketopiperazines and dihydroquinoxalinones," Tetrahedron Letters 39:7227-30 (1998).
International Preliminary Report on Patentability for International Application No. PCT/CA2009/000768, dated Dec. 6, 2010 (7 pages).
International Preliminary Report on Patentability for International Application No. PCT/US2014/019026, dated Sep. 1, 2015 (10 pages).
International Search Report and Written Opinion for International Application No. PCT/CA2009/000768, dated Sep. 11, 2009 (14 pages).
International Search Report and Written Opinion for International Application No. PCT/CA2010/001386, dated Dec. 9, 2010 (18 pages).
International Search Report and Written Opinion for International Application No. PCT/US14/19026, dated Jul. 21, 2014 (18 pages).
Itoh et al., "Synthesis and pharmacological evaluation of carboxamide derivatives as selective serotoninergic 5-HT(4) receptor agonists," Eur J Med Chem. 34:329-41 (1999).
Itoh et al., "Synthesis and pharmacological properties of novel benzamide derivatives acting as ligands to the 5-hydroxytryptamine 4 (5-HT$_4$) receptor," Eur J Med Chem. 34:1101-8 (Laboratory Note) (1999).
Jordan, "Tamoxifen: a most unlikely pioneering medicine," Nat Rev Drug Discov. 2(3):205-13 (2003).
Kim et al., "Altered nociceptive response in mice deficient in the alpha(1B) subunit of the voltage-dependent calcium channel," Mol Cell Neurosci. 18(2):235-45 (2001).

López-Rodríguez et al., "Benzimidazole derivatives. 3. 3D-QSAR/CoMFA model and computational simulation for the recognition of 5-HT(4) receptor antagonists," J Med Chem. 45(22):4806-15 (2002).
López-Rodríguez et al., "3-D-QSAR/CoMFA and recognition models of benzimidazole derivatives at the 5-HT(4) receptor," Bioorg Med Chem Lett. 11(21):2807-11 (2001).
López-Rodríguez et al., "Benzimidazole derivatives. Part 1: Synthesis and structure-activity relationships of new benzimidazole-4-carboxamides and carboxylates as potent and selective 5-HT4 receptor antagonists," Bioorg Med Chem. 7(11):2271-81 (1999).
McCalmont et al., "Design, synthesis, and biological evaluation of novel T-Type calcium channel antagonists," Bioorg Med Chem Lett. 14(14):3691-5 (2004).
McGivern, "Targeting N-type and T-type calcium channels for the treatment of pain," Drug Discov Today. 11(5-6):245-53 (2006).
Miller, "Multiple calcium channels and neuronal function," Science. 235(4784):46-52 (1987).
Moss et al., "A new class of 5-HT2B antagonists possesses favorable potency, selectivity, and rat pharmacokinetic properties," Bioorg Med Chem Lett. 19(8):2206-10 (2009).
Ner et al., "Inhibition of carboxypeptidase by cyclopropane-containing peptides," J Chem Soc Chem Commun. 480-2 (1987).
Office Action for Chinese Application No. 200980129679.1, dated Apr. 29, 2014 (8 pages).
Office Action for Chinese Application No. 200980129679.1, dated Feb. 28, 2013 (21 pages).
Office Action for Chinese Application No. 200980129679.1, dated Nov. 26, 2013 (22 pages).
Office Action for Korean Application No. 10-2010-7028775, dated Sep. 11, 2015 (7 pages).
Office Action for U.S. Appl. No. 12/420,793, dated Aug. 17, 2011 (16 Pages).
Office Action for U.S. Appl. No. 12/420,793, dated Jan. 13, 2011 (10 pages).
Patani et al., "Bioisosterism: A Rational Approach in Drug Design," Chem Rev. 96(8):3147-76 (1996).
Patent Examination Report for Australian Application No. 2009253797, dated Nov. 27, 2012 (4 pages).
Patent Examination Report for European Application No. 09757002.2, dated Feb. 28, 2013 (5 pages).
Pesson et al., "Antibactériens dérivés des acides alkyl-8 dihydro-5,8 oxo-5 pyrido [2,3-d] pyrimidine-6 carboxyliques. III dérivés (aryl-4 pipérazinyl)-2, (aralkyl-4 pipérazinyl)-2 et [(delta2 imidazolinyl-1]-2," Eur J Med Chem. 10(6):567-72 (1975).
Prabhakaran et al., "Synthesis and conformation of proline containing tripeptides constrained with phenylalanine-like aziridine and dehydrophenylalanine residues," Tetrahedron Letters. 43:6461-6 (2002).
Shanklin, Jr. et al., "Synthesis, calcium-channel-blocking activity, and antihypertensive activity of 4-(diarylmethyl)-1-[3-(aryloxy)propyl]piperidines and structurally related compounds," J Med Chem. 34(10):3011-22 (1991).
Shipe et al., "Design, synthesis, and evaluation of a novel 4-aminomethyl-4-fluoropiperidine as a T-type Ca2+ channel antagonist," J Med Chem. 51(13):3692-5 (2008).
Su et al., "Upregulation of a T-type Ca2+ channel causes a long-lasting modification of neuronal firing mode after status epilepticus," J Neurosci. 22(9):3645-55 (2002).
Sui et al., "The association between T-type Ca2+ current and outward current in isolated human detrusor cells from stable and overactive bladders," BJU Int. 99(2):436-41 (2006).
Taylor et al., "Calcium signaling and T-type calcium channels in cancer cell cycling," World J. Gastroenterol. 14(32):4984-91 (2008).
Translation of Office Action for Israeli Application No. 209581, dated Oct. 2, 2013 (4 pages).
Uebele et al., "Antagonism of T-type calcium channels inhibits high-fat diet-induced weight gain in mice," J Clin Invest. 119(6):1659-67 (2009).
Vippagunta et al., "Crystalline solids," Adv Drug Deliv Rev. 48(1):3-26 (2001).
Wolff, *Burger's Medicinal Chemistry and Drug Discovery, 5th Edition*, vol. 1: *Principles and Practice*. John Wiley & Sons, 975-7 (1995) (4 pages).

(56) References Cited

OTHER PUBLICATIONS

Yang et al., "Discovery of 1,4-substituted piperidines as potent and selective inhibitors of T-type calcium channels," J Med Chem. 51(20):6471-7 (2008).

Zechel et al., "Highly potent and selective alphaVbeta3-receptor antagonists: solid-phase synthesis and SAR of 1-substituted 4-amino-1 H-pyrimidin-2-ones," Bioorg Med Chem Lett 13(2):165-9 (2003).

Christopher et al. "A Bioinformatics Search for Selective Histamine H4 Receptor Antagonists Through Structure-Base Virtual Screening Strategies", Chem. Biol. Drug Des., (20120000), vol. 79, No. 5, pp. 749-759, XP055219977 [X] 88-92, 95-100 and 104-108 * pp. 754, 756 *.

International Search Report, PCT/CA2015/000132, dated Jun. 8, 2015.

* cited by examiner

HETEROCYCLIC INHIBITORS OF THE SODIUM CHANNEL

FIELD OF THE INVENTION

The invention relates to compounds useful in treating conditions associated with voltage-gated ion channel function, particularly conditions associated with sodium channel activity. More specifically, the invention relates to heterocyclic compounds (e.g., compounds according to any of Formulas (I)-(X) or Compounds (1)-(92) of Table 1) that are that are useful in treatment of diseases and conditions such as epilepsy, cancer, pain, migraine, Parkinson's Disease, mood disorders, schizophrenia, psychosis, tinnitus, amyotrophic lateral sclerosis, glaucoma, ischemia, spasticity disorders, obsessive compulsive disorder, restless leg syndrome and Tourette syndrome.

BACKGROUND OF THE INVENTION

Voltage-gated sodium (Nav) channels are present in neurons and excitable tissues where they contribute to processes such as membrane excitability and muscle contraction (Ogata et al., *Jpn. J. Pharmacol.* (2002) 88(4), 365-77). Nine different transmembrane β-subunits (Nav1.1-1.9) from a single Nav1 family combine with auxiliary β-subunits that modify channel function to form functional Nav channels. Of the nine Nav1 β-subunit isoforms, five are expressed in the dorsal root ganglion where they are involved in setting the resting membrane potential and the threshold for generating action potentials, and also contribute to the upstroke as well as firing of action potentials during sustained depolarization. In particular, the tetrodotoxin (TTX) sensitive Nav1.7 and TTX-insensitive Nav1.8 channel subtypes act as major contributors to both inflammatory and neuropathic pain (Momin et al., *Curr. Opin. Neurobiol.* 18(4):383-8, 2008; Rush et al., *J. Physiol.* 579(Pt 1):1-14, 2007).

Pathological pain states induce neuronal hyper-excitability in the peripheral and central nervous systems and as a consequence modulate voltage-gated ion channel behavior (Coderre and Katz, *Behav. Brain Sci.* 20(3):404-19, 1997; Hildebrand et al., *Pain.* 152(4):833-843, 2011). In humans, gain-of-function mutations in the Nav1.7 gene, SNC9A, yield the condition of inherited erythromelalgia typified by extreme pain, redness and swelling in the extremities (Drenth and Waxman, *J. Clin. Invest.* 117(12):3603-3609, 2007). These mutations result in amino acid substitutions that alter channel function and induce hyper-excitability of the Nav1.7 channel by allowing the ion channel to open at lower membrane potentials (Cheng et al., *Mol. Pain.* 4(1): 1-9, 2008). Across the various Nav1.7 mutations identified as contributing to erythromelalgia, select mutations result in a reduction of pain severity (Cheng et al., *Brain.* 134(Pt 7):1972-1986, 2011). While these mutations still allow the channel to open at lower membrane potentials, this subset alters the manner in which the ion channel resets to its original closed state so that it can continue to participate in pain signaling. While unmutated Nav1.7 channels reset primarily through a kinetically rapid state on the millisecond timescale (fast-inactivation), erythromelalgia mutations resulting in less pain promote channel resetting through a kinetically slow state on the second time scale (slow-inactivation). By limiting channel availability and further participation in sodium ion gating, enhanced entry into the slow-inactivated state reduces pain signaling.

Novel allosteric modulators of voltage-gated ion channels, e.g., voltage gated sodium channels, are thus desired to promote therapeutic analgesia. Modulators may affect the kinetics and/or the voltage potentials of, e.g., Nav1.7 or Nav1.8, channels. In particular, modulators that affect the state-dependence of voltage gated sodium channels by enhancing entry in the slow-inactivated state may be of particular utility in limiting pain signaling by limiting channel availability.

SUMMARY OF THE INVENTION

The invention relates to compounds useful in conditions modulated by sodium channels.

In a first aspect, the invention features a compound having a structure according to the following formula,

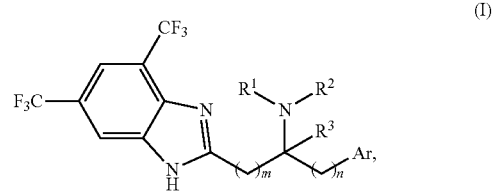

(I)

wherein $R^1$ is H or optionally substituted C1-C6 alkyl; or $R^1$ combines with $R^2$ to form an optionally substituted 5- to 6-membered heterocyclyl; or $R^1$ combines with Ar to form an optionally substituted bicyclic 9- to 10-membered heterocyclyl;

$R^2$ is H or optionally substituted C1-C6 alkyl, or $R^2$ combines with $R^1$ to form an optionally substituted 5- to 6-membered heterocyclyl;

m is 0 or 1;

n is 0 or 1;

$R^3$ is H, optionally substituted C1-C6 alkyl, or optionally substituted phenyl; or $R^3$ combines with $R^1$ to form an optionally substituted 5- to 6-membered heterocyclyl; or $R^3$ combines with Ar to form an optionally substituted bicyclic 9- to 10-membered cycloalkyl or aryl group; and Ar is an optionally substituted phenyl;

or a stereoisomer thereof, or a pharmaceutically acceptable salt thereof.

In certain embodiments, the compound has the structure of Formula I(a):

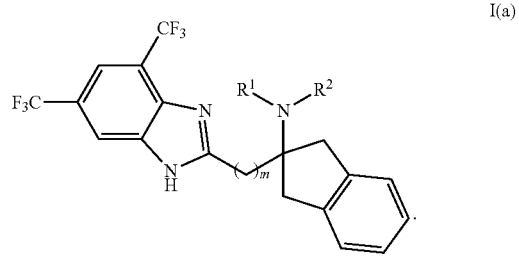

I(a)

In some embodiments, Ar is unsubstituted phenyl, or Ar is phenyl having 1, 2, 3, 4, or 5 substituents selected, independently, optionally substituted C1-C6 alkyl, optionally substituted C1-C6 alkoxy, O-(optionally substituted phenyl), optionally substituted phenyl, —$SO_2$-(optionally substituted phenyl), —$SO_2$-(optionally substituted alkyl), and halogen.

In still other embodiments, Ar includes a halogen substituent.

In further embodiments, $R^1$ and $R^2$ are both H.

In some embodiments, $R^1$ and Ar together form a dihydroindole moiety.

In still other embodiments $R^3$ and Ar together form an indane moiety.

In further embodiments, m is 0 and n is 0.

In some embodiments, m is 1 and n is 0.

In other embodiments, m is 0 and n is 1.

In further embodiments, m is 1 and n is 1.

In yet another embodiment, the compound is selected from compounds 51-59 in Table 1.

In a second aspect, the invention features a compound having a structure according to the following formula,

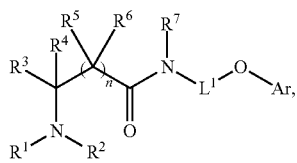

(II)

wherein $R^1$ is H or optionally substituted C1-C6 alkyl; or $R^1$ combines with $R^2$ to form an optionally substituted 5- to 6-membered heterocyclyl; or $R^1$ combines with $R^3$ to form an optionally substituted 5- to 6-membered heterocyclyl; or $R^1$ combines with $R^5$ to form an optionally substituted 5- to 6-membered heterocyclyl;

$R^2$ is H or optionally substituted C1-C6 alkyl, or $R^2$ combines with $R^1$ to form an optionally substituted C5-C6 cycloalkyl or an optionally substituted 5- to 6-membered heterocyclyl;

$R^3$ is H, optionally substituted C1-C6 alkyl, optionally substituted phenyl, or optionally substituted alkaryl; or $R^3$ combines with $R^1$ to form an optionally substituted 5- to 6-membered heterocyclyl; or $R^3$ combines with $R^4$ to form an optionally substituted substituted C3-C6 cycloalkyl or a carbonyl group; or $R^3$ combines with $R^5$ to form an optionally substituted 5- to 6-membered heterocyclyl or an optionally substituted substituted C5-C6 cycloalkyl;

$R^4$ is H or optionally substituted C1-C6 alkyl; or $R^3$ combines with $R^4$ to form an optionally substituted substituted C3-C6 cycloalkyl or a carbonyl group;

n is 0, 1, or 2;

each $R^5$, when present, is independently H or optionally substituted C1-C6 alkyl; or $R^5$ combines with $R^1$ to form an optionally substituted 5- to 6-membered heterocyclyl; or $R^5$ combines with $R^3$ to form an optionally substituted 5- to 6-membered heterocyclyl or an optionally substituted substituted C5-C6 cycloalkyl;

each $R^6$, when present, is independently H or optionally substituted C1-C6 alkyl;

$R^7$ is H or optionally substituted C1-C6 alkyl;

$L^1$ is optionally substituted C1-C6 alkylene; and

Ar is an optionally substituted phenyl;

or a stereoisomer thereof, or a pharmaceutically acceptable salt thereof.

In some embodiments, $R^7$ is H.

In other embodiments, $L^1$ is an optionally substituted C1-C3 alkylene that is linear or branched.

In certain embodiments, the C1-C3 alkylene is unsubstituted.

In other embodiments, $L^1$ is a C1-C3 alkylene comprising an optionally substituted phenyl group.

In some embodiments, -$L^1$-O— is:

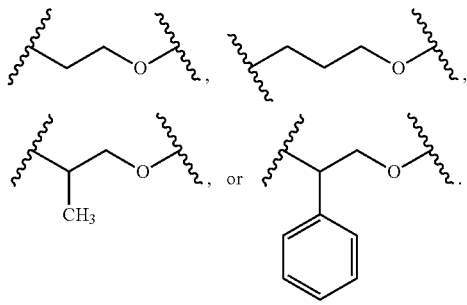

In certain embodiments, $R^1$ is H.

In some embodiments, $R^2$ is H or optionally substituted C1-C2 alkyl.

In other embodiments, $R^1$ and $R^2$ combine to form an unsubstituted 5- to 6-membered heterocyclyl or a 5- to 6-membered heterocyclyl comprising an oxo substitutent.

In other embodiments, $NR^1R^2$ has a structure that is:

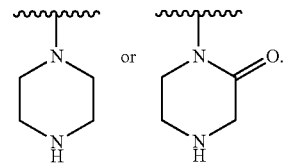 [SMILES: *N1CCNCC1 ; *N1CCNCC1=O]

In yet further embodiments $R^1$ and $R^3$ combine to form to form an unsubstituted 5- to 6-membered heterocyclyl.

In certain embodiments, $R^3$ is H, optionally substituted C1-C6 alkyl, or optionally substituted phenyl.

In some embodiments, $R^4$ is H or unsubstituted C1-C6 alkyl.

In some embodiments, $R^3$ and $R^4$ combine to form:

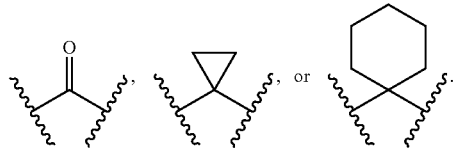

In certain embodiments, n is 0.

In other embodiments, n is 1.

In some embodiments, $R^5$ and $R^6$ are both H.

In still other embodiments, $R^3$ and $R^5$ combine to form an unsubstituted cyclohexyl.

In some embodiments $R^1$ and $R^5$ combine to form an unsubstituted morpholino group.

In other embodiments, n is 2.

In still other embodiments, $R^5$ and $R^6$ are selected from H and optionally substituted C1-C6 alkyl.

In still other embodiments, Ar is phenyl having 1, 2, or 3 substituents selected independently from: optionally substituted C1-C6 alkyl, optionally substituted C1-C6 alkoxy, O-(optionally substituted phenyl), optionally substituted phenyl, —$SO_2$-(optionally substituted phenyl), —$SO_2$-(optionally substituted alkyl), and halogen.

In still other embodiments, Ar is phenyl comprising a substituent that is optionally substituted C1-C6 alkyl or halogen.

In still other embodiments, Ar is substituted with one or more substituents selected from the group consisting of methyl, trifluoromethyl, and fluorine.

In further embodiments, the carbon bearing the —NR$^1$R$^2$ group has the (S)-configuration.

In other embodiments, the carbon bearing the —NR$^1$R$^2$ group has the (R)-configuration.

In still other embodiments, the compound is selected from any one of compounds 1-37 in Table 1.

In a third aspect, the invention features a compound having a structure according to the following formula,

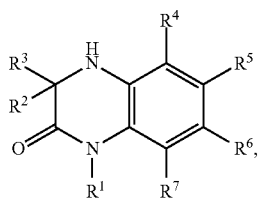

(III)

wherein R$^1$ is selected from hydrogen and optionally substituted C1-C6 alkyl;

R$^2$ and R$^3$ are independently selected from hydrogen; optionally substituted C1-C6 alkyl; optionally substituted C3-C6 cycloalkyl; and optionally substituted aromatic;

each of R$^4$, R$^5$, R$^6$, and R$^7$ is independently selected from H, optionally substituted C1-C6 alkyl, optionally substituted C1 alkoxy, O-(optionally substituted phenyl), optionally substituted phenyl, —SO$_2$-(optionally substituted phenyl), —SO$_2$-(optionally substituted C1-C6 alkyl), and halogen;

or a stereoisomer thereof, or a pharmaceutically acceptable salt thereof.

In some embodiments, R$^1$ is H.

In still other embodiments, R$^3$, R$^5$, and R$^7$ are H.

In further embodiments, R$^2$ is R$^2$ is C1-C6 alkyl that includes an optionally substituted amino group.

In some embodiments, R$^2$ is (CH$_2$)$_m$NH$_2$, wherein m is 1, 2, or 3.

In certain embodiments, R$^4$ and R$^6$ are independently selected from optionally substituted C1-C6 alkyl.

In further embodiments, R$^4$ and R$^6$ are both trifluoromethyl.

In other embodiments, the carbon bearing R$^2$ and R$^3$ has the (S)-configuration.

In still other embodiments, the carbon bearing R$^2$ and R$^3$ has the (R)-configuration.

In other embodiments, the compound is selected from compounds 39-40 in Table 1.

In a fourth aspect, the invention features a compound having a structure according to the following formula,

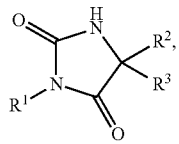

(IV)

wherein R$^1$ is selected from hydrogen and optionally substituted C1-C6 alkyl; and R$^2$ and R$^3$ are independently selected from hydrogen; optionally substituted C1-C6 alkyl; optionally substituted C3-C6 cycloalkyl; and optionally substituted phenyl;

or a stereoisomer thereof, or a pharmaceutically acceptable salt thereof.

In some embodiments, R$^1$ is H.

In still other embodiments, R$^2$ is H or optionally substituted C1-C3 alkyl.

In further embodiments, R$^3$ is optionally substituted phenyl.

In some embodiments, R$^3$ is phenyl having 1 or 2 substituents that are, independently, C1-C3 haloalkyl (e.g., CF$_3$).

In other embodiments, the compound is selected from compounds 41-42 in Table 1.

In a fifth aspect, the invention features a compound having a structure according to the following formula,

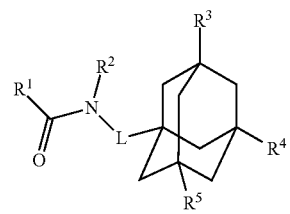

(V)

wherein R$^1$ is an optionally substituted C5-C6 heterocyclyl or optionally substituted C1-C6 aminoalkyl;

R$^2$ is hydrogen or optionally substituted C1-C6 alkyl; and

R$^3$, R$^4$, and R$^5$ are independently selected from optionally substituted C1-C6 alkyl, optionally substituted C1-C6 heteroalkyl, optionally substituted C6-C10 aryl, optionally substituted heteroaryl, and optionally substituted alkaryl;

or a stereoisomer thereof, or a pharmaceutically acceptable salt thereof.

In some embodiments, R$^2$ is H.

In still other embodiments, R$^3$ is H.

In further embodiments, R$^4$ and R$^5$ are independently selected from H and optionally substituted C1-C6 alkyl.

In some embodiments, R$^4$ and R$^5$ are independently selected from H and methyl.

In still other embodiments, R$^1$ is:

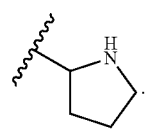 [SMILES: *C1CCCN1]

In further embodiments, R$^1$ is

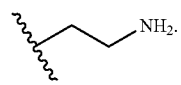

In other embodiments, the compound is selected from compounds 43-46 in Table 1.

In a sixth aspect, the invention features a compound having a structure according to the following formula,

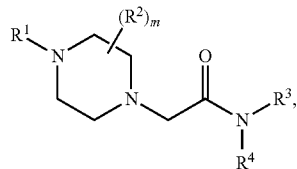
(VI)

wherein R¹ is selected from hydrogen and optionally substituted C1-C6 alkyl;

m is an integer between 0-4 each R² is independently selected from halogen, CN, NO₂, COOR', CONR'₂, OR', SR', SOR', SO₂R', NR'₂, NR'(CO)R', and NR'SO₂R', wherein each R' is independently H or an optionally substituted group selected from C1-C6 alkyl, C2-C6 alkenyl, C2-C6 alkynyl, C2-C6 heteroalkyl, C2-C6 heteroalkenyl, and C2-C6 heteroalkynyl; or each R² is independently an optionally substituted group selected from C1-C6 alkyl, C2-C6 alkenyl, C2-C6 alkynyl, C2-C6 heteroalkyl, C2-C6 heteroalkenyl, or C2-C6 heteroalkynyl; or wherein two R² on the same carbon combine to form =O and =NOR; and R³ and R⁴ are independently selected from hydrogen; optionally substituted C1-C6 alkyl; optionally substituted C3-C6 cycloalkyl; optionally substituted C3-C6 heterocyclyl; SO₂R⁵, wherein R⁵ is amino, optionally substituted C1-C6 alkyl, or optionally substituted phenyl; or R¹ and R² together form an optionally substituted 3- to 7-membered heterocyclyl;

or a stereoisomer thereof, or a pharmaceutically acceptable salt thereof.

In some embodiments, R¹ is H.

In still other embodiments, R⁴ is H.

In further embodiments, m=1.

In some embodiments, R² is =O.

In still other embodiments, R³ is selected from H and optionally substituted C1-C6 alkyl.

In further embodiments, R³ is

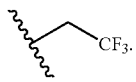

In other embodiments, the compound is compound 47 in Table 1.

In a seventh aspect, the invention features a compound having a structure according to the following formula,

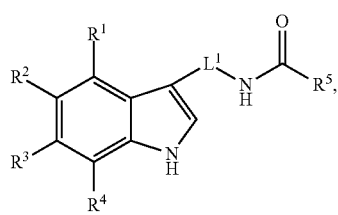
(VII)

wherein R¹, R², R³, and R⁴ are independently selected from H, optionally substituted C1-C6 alkyl, optionally substituted C1-C6 alkoxy, O-(optionally substituted phenyl), optionally substituted phenyl, —SO₂-(optionally substituted phenyl), —SO₂-(optionally substituted C1-C6 alkyl), and halogen;

L¹ is selected from a covalent bond, optionally substituted C1-C3 alkylene, and optionally substituted C1 to C3 heteroalkylene; and R⁵ together with C(O) is an amino acid residue;

or a stereoisomer thereof, or a pharmaceutically acceptable salt thereof.

In some embodiments, L¹ is unsubstituted C1-C3 alkylene.

In still other embodiments, R¹, R³, and R⁴ are H.

In further embodiments, R² is selected from H, optionally substituted C1-C6 alkyl, and halogen.

In some embodiments, R³ is fluorine.

In still other embodiments, R⁵ is

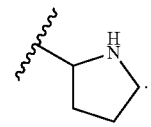

In other embodiments, the compound is compound 48 in Table 1.

In an eighth aspect, the invention features a compound having a structure according to the following formula,

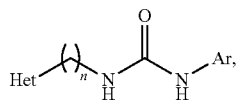
(VIII)

wherein Het is an optionally substituted C3-C6 heterocyclyl;

n is 0 or 1; and

Ar is an optionally substituted phenyl;

or a stereoisomer thereof, or a pharmaceutically acceptable salt thereof.

In some embodiments, Ar is phenyl having a substituent group that is optionally substituted C1-C6 alkyl, optionally substituted C1-C6 alkoxy, O-(optionally substituted phenyl), optionally substituted phenyl, —SO₂-(optionally substituted phenyl), —SO₂-(optionally substituted alkyl), or halogen.

In still other embodiments, Ar is phenyl having a substituent group that is optionally substituted C1-C3 alkyl or optionally substituted C1-C3 alkoxy.

In further embodiments, Ar is phenyl having a substituent group that is trifluoromethyl or trifluoromethoxy.

In some embodiments, n is 0.

In still other embodiments, Het is

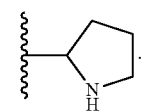

In further embodiments, n is 1.
In some embodiments, Het, is

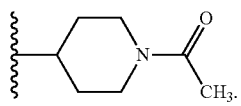

In other embodiments, the compound is selected from compounds 49-50 in Table 1.

In a ninth aspect, the invention features a compound having a structure according to the following formula,

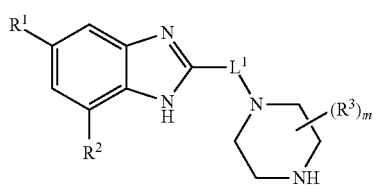

(IX)

wherein $R^1$ and $R^2$ are independently selected from H, optionally substituted C1-C6 alkyl, and halogen;

$L^1$ is optionally substituted C1-C6 alkylene;

m is an integer between 0-4; and each $R^3$ is selected, independently, from halogen, CN, $NO_2$, COOR', CONR'$_2$, OR', SR', SOR', $SO_2$R', NR'$_2$, NR'(CO)R', and NR'$SO_2$R', wherein each R' is independently H or an optionally substituted group selected from C1-C6 alkyl, C2-C6 alkenyl, C2-C6 alkynyl, C2-C6 heteroalkyl, C2-C6 heteroalkenyl, and C2-C6 heteroalkynyl; or each $R^2$ is independently an optionally substituted group selected from C1-C6 alkyl, C2-C6 alkenyl, C2-C6 alkynyl, C2-C6 heteroalkyl, C2-C6 heteroalkenyl, or C2-C6 heteroalkynyl; or wherein two $R^2$ on the same carbon combine to form =O and =NOR;

or a stereoisomer thereof, or a pharmaceutically acceptable salt thereof.

In some embodiments, $L^1$ is selected from:

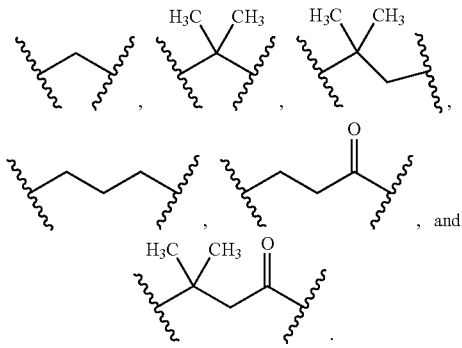

In still other embodiments, $R^1$ and $R^2$ independently selected from H, optionally substituted C1 to C6 alkyl, and halogen.

In further embodiments, m is 0.
In some embodiments, m is 1.
In still other embodiments, $R^3$ is C=O.
In yet another embodiment, the compound is selected from compounds 60-70 in Table 1.

In a tenth aspect, the invention features a compound having a structure according to the following formula,

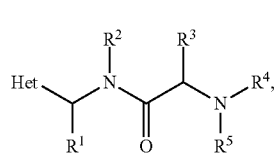

(X)

wherein Het is optionally substituted phenyl, optionally substituted pyridine, or optionally substituted benzimidazole;

$R^1$ is H or optionally substituted C1 to C6 alkyl;

$R^2$ is H, optionally substituted C1 to C6 alkyl, or optionally substituted C1 to C6 alkoxy;

$R^3$ is H, optionally substituted C1 to C6 alkyl, optionally substituted C1 to C6 alkoxy, or optionally substituted phenyl; or $R^3$ combines with $R^4$ to form an optionally substituted 5- to 6-membered heterocyclyl;

$R^4$ is H or optionally substituted C1-C6 alkyl; or $R^4$ combines with $R^5$ to form an optionally substituted 5- to 6-membered heterocyclyl; or $R^4$ combines with $R^3$ to form an optionally substituted 5- to 6-membered heterocyclyl; and $R^5$ is H or optionally substituted C1-C6 alkyl, or $R^5$ combines with $R^4$ to form an optionally substituted C5-C6 cycloalkyl or an optionally substituted 5- to 6-membered heterocyclyl;

or a stereoisomer thereof, or a pharmaceutically acceptable salt thereof.

In some embodiments, Het is selected from:

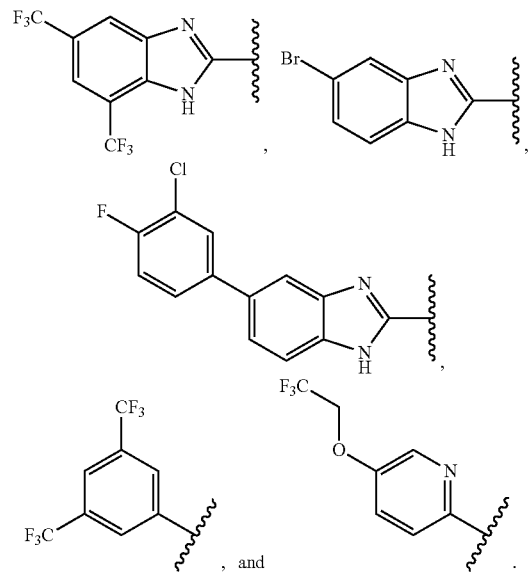

In still other embodiments, $R^1$ and $R^2$ are independently selected from H and methyl.

In further embodiments, $R^4$ is H.

In some embodiments $R^5$ is H or optionally substituted C1-C6 alkyl.

In still other embodiments, R⁴ and R⁵ combine to form:

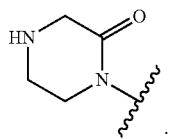

In other embodiments, R³ and R⁴ combine to form:

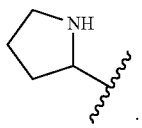

In yet another embodiment, the compound is selected from compounds 71-83 in Table 1.

In an eleventh aspect, the invention is a compound selected from compounds 84-92 in Table 1.

In a twelfth aspect, the invention features a pharmaceutical composition that includes any of the compounds described herein (e.g., a compound according to any of Formulas (I)-(X) or any of Compounds (1)-(92) of Table 1) and a pharmaceutically acceptable carrier or excipient.

In some embodiments, the pharmaceutical composition is formulated in unit dosage form (e.g., a tablet, caplet, capsule, lozenge, film, strip, gelcap, or syrup).

In a thirteenth aspect, the invention features method to treat a disease or condition by administering to a subject in need of such treatment an effective amount of any of the compounds described herein (e.g., a compound according to any of Formulas (I)-(X) or any of Compounds (1)-(92) of Table 1), or a pharmaceutical composition thereof. In some embodiments, the condition is pain, epilepsy, Parkinson's disease, a mood disorder (e.g., a major depressive disorder (e.g., atypical depression, melancholic depression, psychotic major depression, catatonic depression, postpartum depression, seasonal affective disorder, dysthymia, and depressive disorder not otherwise specified (DD-NOS)), recurrent brief depression, minor depressive disorder, or a bipolar disorder), psychosis (e.g., schizophrenia), tinnitus, amyotrophic lateral sclerosis, glaucoma, ischemia, spasticity disorders, obsessive compulsive disorder, restless leg syndrome, and Tourette syndrome.

In particular embodiments, the condition is pain or epilepsy.

In some embodiments, the pain is inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis) or neuropathic pain.

In certain embodiments, the pain is chronic pain.

In further embodiments, the chronic pain is peripheral neuropathic pain; central neuropathic pain, musculoskeletal pain, headache, visceral pain, or mixed pain.

In some embodiments, the peripheral neuropathic pain is post-herpetic neuralgia, diabetic neuropathic pain, neuropathic cancer pain, HIV-associated neuropathy, erythromelalgia, failed back-surgery syndrome, trigeminal neuralgia, or phantom limb pain; said central neuropathic pain is multiple sclerosis related pain, Parkinson disease related pain, post-stroke pain, post-traumatic spinal cord injury pain, lumbosacral radiculopathy, cervical radiculopathy, brachial radiculopathy, or pain in dementia; the musculoskeletal pain is osteoarthritic pain and fibromyalgia syndrome; inflammatory pain such as rheumatoid arthritis, or endometriosis; the headache is migraine, cluster headache, tension headache syndrome, facial pain, or headache caused by other diseases; the visceral pain is interstitial cystitis, irritable bowel syndrome, or chronic pelvic pain syndrome; or the mixed pain is lower back pain, neck and shoulder pain, burning mouth syndrome, or complex regional pain syndrome.

In a fourteenth aspect, the invention features a method of modulating a voltage-gated ion channel (e.g., a voltage-gated sodium channel), where the method includes contacting a cell with any of the compounds described herein (e.g., a compound according to any of Formulas (I)-(X) or any of Compounds (1)-(92) of Table 1).

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like.

Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein. For example, the term "aminoalkyl" refers to an alkyl group, as defined herein, comprising an optionally substituted amino group (e.g., NH₂).

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In some embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In some embodiments, the heteroatom is O or N. The term "heterocyclyl," as used herein represents cyclic heteroalkyl or heteroalkenyl that is, e.g., a 3-, 4-, 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like.

The designated number of carbons in heteroforms of alkyl, alkenyl and alkynyl includes the heteroatom count. For example, if heteroalkyl is defined as C1-C6, it will contain 1-6 C, N, O, or S atoms such that the heteroalkyl contains at least one C atom and at least one heteroatom, for example 1-5 carbons and 1 N atom, or 1-4 carbons and 2 N atoms. Similarly, when heteroalkyl is defined as C1-C6 or C1-C4, it would contain 1-5 carbons or 1-3 carbons respectively, i.e., at least one C is replaced by 0, N or S. Accordingly, when heteroalkenyl or heteroalkynyl is defined as C2-C6 (or C2-C4), it would contain 2-6 or 2-4 C, N, O, or S atoms, since the heteroalkenyl or heteroalkynyl contains at least one carbon atom and at least one heteroatom, e.g. 2-5 carbons and 1 N atom, or 2-4 carbons, and 2 O atoms. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_n NR_2$, OR, COOR, $CONR_2$, $(CH_2)_nOR$, $(CH_2)_n COR$, $(CH_2)_n COOR$, $(CH_2)_nSR$, $(CH_2)_nSOR$, $(CH_2)_nSO_2R$, $(CH_2)_n CONR_2$, NRCOR, NRCOOR, $OCONR_2$, OCOR and the like wherein the R group contains at least one C and the size of the substituent is consistent with the definition of e.g., alkyl, alkenyl, and alkynyl, as described herein (e.g., n is 1, 2, 3, 4, 5, 6, 7, 8, 9, 10, 11, or 12).

As used herein, the terms "alkylene," "alkenylene," and "alkynylene," or the prefix "alk" refer to divalent or trivalent groups having a specified size, typically C1-C2, C1-C3, C1-C4, C1-C6, or C1-C8 for the saturated groups (e.g., alkylene or alk) and C2-C3, C2-C4, C2-C6, or C2-C8 for the unsaturated groups (e.g., alkenylene or alkynylene). They include straight-chain, branched-chain and cyclic forms as well as combinations of these, containing only C and H when unsubstituted. Because they are divalent, they can link together two parts of a molecule, as exemplified by X in the compounds described herein. Examples are methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example. For example, the term "alkaryl," as used herein, represents an aryl group, as defined herein, attached to the parent molecular group through an alkylene group, as defined herein, and the term "alkheteroaryl" refers to a heteroaryl group, as defined herein, attached to the parent molecular group through an alkylene group, as defined herein. The alkylene and the aryl or heteroaryl group are each optionally substituted as described herein.

Heteroalkylene, heteroalkenylene and heteroalkynylene are similarly defined as divalent groups having a specified size, typically C1-C3, C1-C4, C1-C6, or C1-C8 for the saturated groups and C2-C3, C2-C4, C2-C6, or C2-C8 for the unsaturated groups. They include straight chain, branched chain and cyclic groups as well as combinations of these, and they further contain at least one carbon atom but also contain one or more O, S or N heteroatoms or combinations thereof within the backbone residue, whereby each heteroatom in the heteroalkylene, heteroalkenylene or heteroalkynylene group replaces one carbon atom of the alkylene, alkenylene or alkynylene group to which the heteroform corresponds. As is understood in the art, these heteroforms do not contain more than three contiguous heteroatoms.

The term "alkoxy" represents a chemical substituent of formula —OR, where R is an optionally substituted alkyl group (e.g., C1-C6 alkyl group), unless otherwise specified. In some embodiments, the alkyl group can be substituted, e.g., the alkoxy group can have 1, 2, 3, 4, 5 or 6 substituent groups as defined herein.

The term "alkoxyalkyl" represents a heteroalkyl group, as defined herein, that is described as an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. In a preferred embodiment, amino is $—NH_2$, or $—NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl. The term "aminoalkyl," as used herein, represents a heteroalkyl group, as defined herein, that is described as an alkyl group, as defined herein, substituted by an amino group, as defined herein. The alkyl and amino each can be further substituted with 1, 2, 3, or 4 substituent groups as described herein for the respective group. For example, the alkyl moiety may comprise an oxo (=O) substituent.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, isoxazolyl, benzoxazolyl, benzoisoxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, pyridyl, indolyl, pyrimidyl, pyridazinyl, benzothiazolyl, benzimidazolyl, pyrazolyl, imidazolyl, isoxazolyl, thiazolyl, benzothiazolyl, indolyl, or imidazopyridinyl. Even more particularly, such moiety is phenyl, pyridyl, thiazolyl, imidazopyridinyl, or pyrimidyl and even more particularly, it is phenyl.

"O-aryl" or "O-heteroaryl" refers to aromatic or heteroaromatic systems which are coupled to another residue through an oxygen atom. A typical example of an O-aryl is phenoxy. Similarly, "arylalkyl" refers to aromatic and heteroaromatic systems which are coupled to another residue through a carbon chain, saturated or unsaturated, typically of C1-C8, C1-C6, or more particularly C1-C4 or C1-C3 when saturated or C2-C8, C2-C6, C2-C4, or C2-C3 when unsaturated, including the heteroforms thereof. For greater certainty, arylalkyl thus includes an aryl or heteroaryl group as defined above connected to an alkyl, heteroalkyl, alkenyl, heteroalkenyl, alkynyl or heteroalkynyl moiety also as defined above. Typical arylalkyls would be an aryl(C6-C12)alkyl(C1-C8), aryl(C6-C12)alkenyl(C2-C8), or aryl(C6-C12)alkynyl(C2-C8), plus the heteroforms. A typical example is phenylmethyl, commonly referred to as benzyl.

Halo may be any halogen atom, especially F, Cl, Br, or I, and more particularly it is fluoro or chloro.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls. In some embodiments, the haloalkyl group can be further substituted with 1, 2, 3, or 4 substituent groups as described herein for alkyl groups.

The term "hydroxy," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

An "oxo" group is a substituent having the structure C=O, where there is a double bond between a carbon and an oxygen atom.

Typical optional substituents on aromatic or heteroaromatic groups include, independently, halo, CN, $NO_2$, $CF_3$, $OCF_3$, COOR', $CONR'_2$, OR', SR', SOR', $SO_2R'$, $NR'_2$, NR'(CO)R', NR'C(O)OR', NR'C(O)$NR'_2$, NR'$SO_2NR'_2$, or NR'$SO_2$R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, C1-C6 alkyl or heteroaryl, C2-C6 alkenyl or heteroalkenyl, C2-C6 alkynyl or heteroalkynyl, aryl, or heteroaryl. A substituted group may have, for example, 1, 2, 3, 4, 5, 6, 7, 8, or 9 substituents.

In some embodiments, the invention features moieties that are amino acid residues. The amino acid residue may be of a naturally occurring amino acid (e.g., Ala, Arg, Asn, Asp, Cys, Gln, Glu, Gly, His, Ile, Leu, Lys, Met, Phe, Pro, Ser, Thr, Trp, Tyr, or Val), or the amino acid residue may be of a non-naturally occurring amino acid. A "non-naturally occurring amino acid" is an amino acid which is not naturally produced or found in a mammal. Examples of non-naturally occurring amino acids include D-amino acids; an amino acid having an acetylaminomethyl group attached to a sulfur atom of a cysteine; a pegylated amino acid; the omega amino acids of the formula $NH_2(CH_2)_n$COOH wherein n is 2-6, neutral nonpolar amino acids, such as sarcosine, t-butyl alanine, t-butyl glycine, N-methyl isoleucine, and norleucine; phenylglycine; citrulline; methionine sulfoxide; cysteic acid; ornithine; and hydroxyproline.

The term an "effective amount" of an agent (e.g., a compound according to any of Formulas (I)-(X) or any of Compounds (1)-(92) of Table 1), as used herein, is that amount sufficient to effect beneficial or desired results, such as clinical results, and, as such, an "effective amount" depends upon the context in which it is being applied. For example, in the context of administering an agent that is a modulator of a sodium channel (e.g., Nav1.7 or Nav1.8), an effective amount of an agent is, for example, an amount sufficient to achieve a change in sodium channel activity as compared to the response obtained without administration of the agent.

The term "pharmaceutical composition," as used herein, represents a composition containing a compound described herein (e.g., a compound according to any of Formulas (I)-(X) or any of Compounds (1)-(92) in Table 1) formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention that are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts of the compounds described here (e.g., a compound according to any of Formulas (I)-(X) or any of Compounds (1)-(92) in Table 1) that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable solvate" as used herein means a compound as described herein (e.g., a compound according to any of Formulas (I)-(X) or any of Compounds (1)-(92) in Table 1) where molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "prevent," as used herein, refers to prophylactic treatment or treatment that prevents one or more symptoms or conditions of a disease, disorder, or conditions described herein (for example, pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control). Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein (e.g., a compound according to any of Formulas (I)-(X) or any of Compounds (1)-(92) in Table 1), or a pharmaceutically acceptable salt or solvate thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic (C1-C8 or C8-C24) esters, cholesterol esters, acyloxymethyl esters, carbamates, and amino acid esters. For example, a compound that contains an OH group may be acylated at this position in its prodrug form. A thorough discussion is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to compounds (e.g., a compound according to any of Formulas (I)-(X) or any of Compounds (1)-(92) in Table 1) when modified so as to be included in a conjugate of this type.

As used herein, and as well understood in the art, "to treat" a condition or "treatment" of the condition (e.g., the conditions described herein such as pain (e.g., chronic or acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, and syrup.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers, enantiomers, and tautomers that can be formed.

Compounds useful in the invention may also be isotopically labeled compounds. Useful isotopes include hydrogen, carbon, nitrogen, oxygen, phosphorous, fluorine, and chlorine, (e.g., $^2$H, $^3$H, $^{13}$C, $^{15}$N, $^{18}$O, $^{17}$O, $^{31}$P, $^{32}$P, $^{35}$S, $^{18}$F, and $^{35}$Cl). Isotopically labeled compounds can be prepared by synthesizing a compound using a readily available isotopically labeled reagent in place of a non-isotopically labeled reagent. In some embodiments, the compound (e.g., a compound according to any of Formulas (I)-(X) or any of Compounds (1)-(92) in Table 1), or a composition that includes the compound, has the natural abundance of each element present in the compound.

Other features and advantages of the invention will be apparent from the following Detailed Description and the claims.

The compounds described herein (e.g., a compound according to any of Formulas (I)-(X) or any of Compounds (1)-(92) of Table 1) are also useful for the manufacture of a medicament useful to treat conditions requiring modulation of voltage-gated ion channel, e.g., sodium channel activity, and in particular Nav1.7 or Nav1.8 channel activity, or any combination thereof.

Other features and advantages of the invention will be apparent from the following detailed description, the drawings, and the claims.

DETAILED DESCRIPTION OF THE INVENTION

Compounds

The invention features compounds that can inhibit voltage-gated ion channel activity (e.g., voltage-gated sodium channels) by state-dependent enhancement of slow-inactivation and other use-dependent mechanisms. Exemplary compounds described herein include compounds having a structure according the following formulae (I)-(X) as described herein:

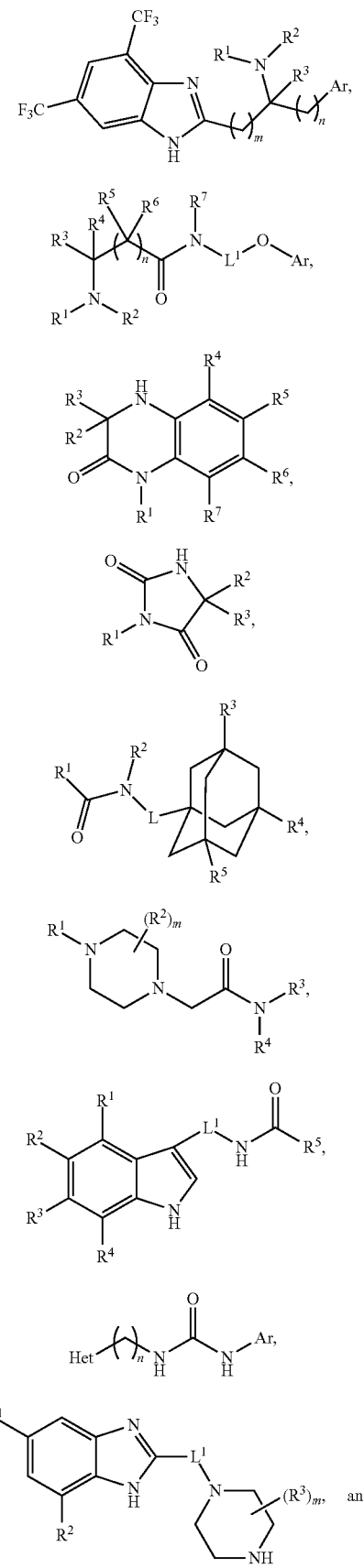

or a stereoisomer thereof, or a pharmaceutically acceptable salt thereof.

Other embodiments (e.g., Compounds (1)-(92) of Table 1), as well as exemplary methods for the synthesis of these compounds, are described herein.

Utility and Administration

The compounds described herein (e.g., a compound according to any of Formulas (I)-(X) or any of Compounds (1)-(92) of Table 1) are useful in the methods of the invention and, while not bound by theory, are believed to exert their desirable effects through their ability to modulate the activity of voltage-gated ion channels, e.g., sodium channels such as the Nav1.7 and Nav1.8 channels. The compounds described herein (e.g., a compound according to any of Formulas (I)-(X) or any of Compounds (1)-(92) of Table 1) can also be used for the treatment of certain conditions such as pain, epilepsy, migraine, Parkinson's disease, mood disorders, schizophrenia, psychosis, tinnitus, amyotrophic lateral sclerosis, glaucoma, ischaemia, spasticity disorders, obsessive compulsive disorder, restless leg syndrome, and Tourette syndrome.

Modulation of Sodium Channels

There are nine Nav1 β-subunit isoforms: Nav1.1-1.9 (see, e.g., Yu et al., *Genome Biolog,* 4:207, 2003). In addition to pain, other conditions associated with voltage-dependent sodium channel activity include seizures (e.g., Nav1.1), epilepsy (e.g., Nav1.2), neurodegeneration (e.g., Nav1.1, Nav1.2), myotonia (e.g., Nav1.4), arrhythmia (e.g., Nav1.5), and movement disorders (e.g., Nav1.6) as described in PCT Publication No. WO 2008/118758, herein incorporated by reference. The expression of particular isoforms in particular tissues can influence the therapeutic effects of sodium channel modulators. For example, the Nav1.4 and Nav1.5 isoforms are largely found in skeletal and cardiac myocytes (see, e.g., Gold, *Exp. Neurol.* 210(1): 1-6, 2008).

Sodium Channel Activity and Pain

Voltage-dependent ion channels in pain-sensing neurons are currently of great interest in developing drugs to treat pain. For example, blocking voltage-dependent sodium channels in pain-sensing neurons can block pain signals by interrupting initiation and transmission of the action potential. Studies also indicate that particular sodium channel isoforms are predominantly expressed in peripheral sensory neurons associated with pain sensation; for example, Nav1.7, Nav1.8 and Nav1.9 activity are thought to be involved in inflammatory, and possibly neuropathic, pain (see, e.g., Cummins et al., *Pain,* 131(3):243-257, 2007). The Nav1.3 isoform has also been implicated in pain, e.g., pain associated with tissue injury (Gold, *Exp. Neurol.* 210(1): 1-6, 2008).

The Nav1.7 and Nav1.8 channel subtypes act as major contributors to both inflammatory and neuropathic pain (vide infra). Recently, mutations have been identified in the Nav1.7 channel that lead either to a gain of channel function (Dib-Hajj et al., *Brain* 128:1847-1854, 2005) or more commonly to a loss of channel function (Chatelier et al., *J. Neurophysiol.* 99:2241-50, 2008). These mutations underlie human heritable disorders such as erythromelalgia (Yang et al., *J. Med. Genet.* 41(3) 171-4, 2004), paroxysmal extreme pain disorder (Fertleman et al., *Neuron.* 52(5) 767-74, 2006), and congenital indifference to pain (Cox et al., *Nature* 444(7121):894-8, 2006). Behavioral studies have shown in mice that inflammatory and acute mechanosensory pain is reduced when Nav1.7 is knocked out in Nav1.8-positive neurons (Nassar et al., *Proc. Natl. Acad. Sci. USA.* 101(34): 12706-11, 2004). In addition, siRNA of Nav1.7 attenuates inflammatory hyperalgesia (Yeomans et al., *Hum Gene Ther.* 16(2) 271-7, 2005).

The Nav1.8 isoform is selectively expressed in sensory neurons and has been identified as a target for the treatment of pain, e.g., chronic pain (e.g., Swanwick et al., *Neurosci. Lett.* 486:78-83, 2010). The role of Nav1.8 in inflammatory (Khasar et al. *Neurosci. Lett.* 256(1):17-20, 1998), neuropathic and mechanical hyperalgesia (Joshi et al., *Pain* 123 (1-2):75-82, 2006) has also emerged using molecular techniques to knockdown Nav1.8, which has been shown to reduce the maintenance of these different pain states.

Lacosamide is a functionalized amino acid that has shown effectiveness as an analgesic in several animal models of neuropathic pain and is currently in late stages of clinical development for epilepsy and diabetic neuropathic pain. One mode of action that has been validated for lacosamide is inhibition of voltage-gated sodium channel activity by selective inhibition with the slow-inactivated conformation of the channel (Sheets et al., *Journal of Pharmacology and Experimental Therapeutics,* 326(1) 89-99 (2008)). Modulators of sodium channels, including clinically relevant compounds, can exhibit a pronounced state-dependent binding, where sodium channels that are rapidly and repeatedly activated and inactivated are more readily blocked. In a simplified scheme, voltage-gated sodium channels have four distinct states: open, closed, fast-inactivated and slow-inactivated. Classic sodium channel modulators, such as lidocaine, are believed to exhibit the highest affinity for the fast-inactivated state. However, alteration of the slow inactivated state is also clinically relevant. As demonstrated by gain-of-function mutations of the Nav1.7 gene, SCN9A, a subset of mutations that promote entry of the Nav1.7 channel into the slow inactivated state result in less severe forms of erythromelalgia (Cheng et al., *Brain.* 134(Pt 7):1972-1986, 2011). Because repeated Nav1.7 channel activation results in greater proportions of the channel to be in the slow inactivated state and further stabilization of the channel in the slow-inactivated state limits pain, the identification of modulators that enhance ion channel entry into the slow inactivated state would be believed to produce a therapeutic analgesic effect (Blair and Bean, *J Neurosci.* 23(32):10338-20350, 2003).

The modulation of ion channels by the compounds described herein (e.g., a compound according to any of Formulas (I)-(X) or any of Compounds (1)-(92) of Table 1) can be measured according to methods known in the art (e.g., in the references provided herein) to monitor both use- and state-dependence (Tables 2 and 3). This electrophysiological data can be used to further characterize the modulators as enhancers of slow inactivation (Table 3). Modulators of ion channels, e.g., voltage gated sodium ion channels, and the medicinal chemistry or methods by which such compounds can be identified, are also described in, for example: Birch et al., *Drug Discovery Today,* 9(9):410-418 (2004); Audesirk, "Chapter 6-Electrophysiological Analysis of Ion Channel Function," *Neurotoxicology: Approaches and Methods,* 137-156 (1995); Camerino et al., "Chapter 4: Therapeutic Approaches to Ion Channel Diseases," *Advances in Genetics,* 64:81-145 (2008); Petkov, "Chapter 16-Ion Channels," *Pharmacology: Principles and Practice,* 387-427 (2009); Standen et al., "Chapter 15-Patch Clamping Methods and Analysis of Ion Channels," *Principles of Medical Biology,* Vol. 7, Part 2, 355-375 (1997); Xu et al., *Drug Discovery Today,* 6(24):1278-1287 (2001); and Sullivan et al., *Methods Mol. Biol.* 114:125-133 (1999). Exemplary experimental methods are also provided in the Examples.

Diseases and Conditions

Exemplary conditions that can be treated using the compounds described herein include pain (e.g., chronic or acute pain), epilepsy, Alzheimer's disease, Parkinson's disease, diabetes; cancer; sleep disorders; obesity; psychosis such as schizophrenia; overactive bladder; renal disease, neuroprotection, and addiction. For example, the condition can be pain (e.g., neuropathic pain or post-surgery pain), epilepsy, migraine, Parkinson's disease, mood disorders, schizophrenia, psychosis, tinnitus, amyotrophic lateral sclerosis, glaucoma, ischemia, spasticity disorders, obsessive compulsive disorder, restless leg syndrome and Tourette syndrome.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adrenocarcinoma, insulinoma, lung carcinoma, melanoma, and ovarian cancer.

Acute pain as used herein includes but is not limited to nociceptive pain and post-operative pain. Chronic pain includes but is not limited by: peripheral neuropathic pain (e.g., post-herpetic neuralgia, diabetic neuropathic pain, neuropathic cancer pain, HIV-associated neuropathy, erythromelalgia, failed back-surgery syndrome, trigeminal neuralgia, or phantom limb pain); central neuropathic pain (e.g., multiple sclerosis related pain, Parkinson disease related pain, post-stroke pain, post-traumatic spinal cord injury pain, lumbosacral radiculopathy, cervical radiculopathy, brachial radiculopathy, or pain in dementia); musculoskeletal pain such as osteoarthritic pain and fibromyalgia syndrome; inflammatory pain (e.g., inflammatory pain caused by rheumatoid arthritis, juvenile idiopathic arthritis, ankylosing spondylitis, psoriatic arthritis, inflammatory bowel disease, primary dysmenorrhea, or endometriosis); headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

In treating osteoarthritic pain, joint mobility can also improve as the underlying chronic pain is reduced. Thus, use of compounds of the present invention to treat osteoarthritic pain inherently includes use of such compounds to improve joint mobility in patients suffering from osteoarthritis.

The compounds described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compounds (Stein et al., *Pharmacol. Biochem. Behav.* (1988) 31: 445-451; Woolf et al., *Neurosci.* (1994) 62: 327-331). Additionally, various tests assess peripheral neuropathic pain using lesions of the peripheral nervous system. One such example is the "axotomy pain model" (Watson, *J. Physiol.* (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCI) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischemia to a nerve, peripheral neuritis models (e.g., CFA applied perineurally), models of post-herpetic neuralgia using HSV infection, and compression models.

In all of the above tests, outcome measures may be assessed, for example, according to behavior, electrophysiology, neurochemistry, or imaging techniques to detect changes in neural activity.

Exemplary disease models include, but are not limited to, the following models described below.

Pain Models

L5/L6 Spinal Nerve Ligation (SNL)—Chung Pain Model

The Spinal Nerve Ligation is an animal model representing peripheral nerve injury generating a neuropathic pain syndrome. In this model experimental animals develop the clinical symptoms of tactile allodynia and hyperalgesia. L5/L6 Spinal nerve ligation (SNL) injury was induced using the procedure of Kim and Chung (Kim et al., *Pain* 50:355-363 (1992)) in male Sprague-Dawley rats (Harlan; Indianapolis, Ind.). An exemplary protocol is provided below.

Animals can be anesthetized with isoflurane, and the left L6 transverse process can be removed, and the L5 and L6 spinal nerves can be tightly ligated with 6-0 silk suture. The wound can then be closed with internal sutures and external tissue adhesive. Rats that exhibit motor deficiency (such as paw-dragging) or failure to exhibit subsequent tactile allodynia can be excluded from further testing.

Sham control rats can undergo the same operation and handling as the experimental animals, but without SNL.

Assessment of Mechanical Hyperalgesia

Baseline and post-treatment values for mechanical hyperalgesia can be evaluated using a digital Randall-Selitto device (dRS; IITC Life Sciences, Woodland Hills, Calif.). Animals can be allowed to acclimate to the testing room for a minimum of 30 minutes before testing. Animals can be placed in a restraint sling that suspends the animal, leaving the hind limbs available for testing. Paw compression threshold was measured once at each time point for the ipsilateral and contralateral paws. The stimulus can be applied to the plantar surface of the hind paw by a dome-shaped tip placed between the 3rd and 4th metatarsus, and pressure can be applied gradually over approximately 10 seconds. Measurements can be taken from the first observed nocifensive behavior of vocalization, struggle or withdrawal. A cut-off value of 300 g can be used to prevent injury to the animal. The mean and standard error of the mean (SEM) can be determined for each paw for each treatment group. Fourteen days after surgery, mechanical hyperalgesia can be assessed, and rats can be assigned to treatment groups based on pre-treatment baseline values. Prior to initiating drug delivery, baseline behavioral testing data can be obtained. At selected times after infusion of the Test or Control Article behavioral data can then be collected again.

Assessment of Tactile Allodynia—Von Frey

The assessment of tactile allodynia can consist of measuring the withdrawal threshold of the paw ipsilateral to the site of nerve injury in response to probing with a series of calibrated von Frey filaments (innocuous stimuli). Animals can be acclimated to the suspended wire-mesh cages for 30 min before testing. Each von Frey filament can be applied perpendicularly to the plantar surface of the ligated paw of rats for 5 sec. A positive response can be indicated by a sharp withdrawal of the paw. For rats, the first testing filament is 4.31. Measurements can be taken before and after administration of test articles. The paw withdrawal threshold can be determined by the non-parametric method of Dixon (Dixon, *Ann. Rev. Pharmacol. Toxicol.* 20:441-462 (1980)), in which the stimulus was incrementally increased until a positive response was obtained, and then decreased until a negative result was observed. The protocol can be repeated until three changes in behavior were determined ("up and down" method; Chaplan et al., *J. Neurosci. Methods* 53:55-63 (1994)). The 50% paw withdrawal threshold can be determined as $(10^{[Xf+k\delta]})/10,000$, where $X_f$=the value of the last von Frey filament employed, k=Dixon value for the positive/negative pattern, and $\delta$=the logarithmic difference between stimuli. The cut-off values for rats can be, for example, no less than 0.2 g and no higher than 15 g (5.18 filament); for mice no less than 0.03 g and no higher than 2.34 g (4.56 filament). A significant drop of the paw withdrawal threshold compared to the pre-treatment baseline is considered tactile allodynia. Rat SNL tactile allodynia can be tested for the compounds described herein at, e.g., 60 minutes compared to baseline and post-SNL.

Assessment of Thermal Hypersensitivity—Hargreaves

The method of Hargreaves and colleagues (Hargreaves et al., *Pain* 32:77-8 (1988)) can be employed to assess paw-withdrawal latency to a noxious thermal stimulus.

Rats may be allowed to acclimate within a Plexiglas enclosure on a clear glass plate for 30 minutes. A radiant heat source (e.g., halogen bulb coupled to an infrared filter) can then be activated with a timer and focused onto the plantar surface of the affected paw of treated rats. Paw-withdrawal latency can be determined by a photocell that halts both lamp and timer when the paw is withdrawn. The latency to withdrawal of the paw from the radiant heat source can be determined prior to L5/L6 SNL, 7-14 days after L5/L6 SNL but before drug, as well as after drug administration. A maximal cut-off of 33 seconds is typically employed to prevent tissue damage. Paw withdrawal latency can be thus determined to the nearest 0.1 second. A significant drop of the paw withdrawal latency from the baseline indicates the status of thermal hyperalgesia. Antinociception is indicated by a reversal of thermal hyperalgesia to the pre-treatment baseline or a significant (p<0.05) increase in paw withdrawal latency above this baseline.

Data is converted to % anti hyperalgesia or % anti nociception by the formula: (100×(test latency−baseline latency)/(cut-off−baseline latency) where cut-off is 21 seconds for determining anti hyperalgesia and 40 seconds for determining anti nociception.

Epilepsy Models
6 Hz Psychomotor Seizure Model of Partial Epilepsy

Compounds can be evaluated for the protection against seizures induced by a 6 Hz, 0.2 ms rectangular pulse width of 3 s duration, at a stimulus intensity of 32 mA (CC97) applied to the cornea of male CF1 mice (20-30 g) according to procedures described by Barton et al, "Pharmacological Characterization of the 6 Hz Psychomotor Seizure Model of Partial Epilepsy," *Epilepsy Res.* 47(3):217-27 (2001). Seizures are characterized by the expression of one or more of the following behaviors: stun, forelimb clonus, twitching of the vibrissae and Straub-tail immediately following electrical stimulation. Animals can be considered "protected" if, following pre-treatment with a compound, the 6 Hz stimulus failed to evoke a behavioral response as describe above.

Assessments of Neurological or Muscular Impairments

To assess a compound's undesirable side effects (toxicity), animals can be monitored for overt signs of impaired neurological or muscular function. In mice, the rotarod procedure (Dunham et al., *J. Am. Pharmacol. Assoc.* 46:208-209 (1957)) is used to disclose minimal muscular or neurological impairment (MMI). When a mouse is placed on a rod that rotates at a speed of 6 rpm, the animal can maintain its equilibrium for long periods of time. The animal is considered toxic if it falls off this rotating rod three times during a 1-min period. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

Recordings on Lamina I/II Spinal Cord Neurons

Male Wistar rats (P6 to P9 for voltage-clamp and P15 to P18 for current-clamp recordings) can be anaesthetized through intraperitoneal injection of Inactin (Sigma). The spinal cord can then be rapidly dissected out and placed in an ice-cold solution protective sucrose solution containing (in mM): 50 sucrose, 92 NaCl, 15 D-Glucose, 26 $NaHCO_3$, 5 KCl, 1.25 $NaH_2PO_4$, 0.5 $CaCl_2$, 7 $MgSO_4$, 1 kynurenic acid, and bubbled with 5% $CO_2$/95% $O_2$. The meninges, dura, and dorsal and ventral roots can then removed from the lumbar region of the spinal cord under a dissecting microscope. The "cleaned" lumbar region of the spinal cord may be glued to the vibratome stage and immediately immersed in ice cold, bubbled, sucrose solution. For current-clamp recordings, 300 to 350 μm parasagittal slices can be cut to preserve the dendritic arbour of lamina I neurons, while 350 to 400 μm transverse slices can be prepared for voltage-clamped Nav channel recordings. Slices may be allowed to recover for 1 hour at 35° C. in Ringer solution containing (in mM): 125 NaCl, 20 D-Glucose, 26 $NaHCO_3$, 3 KCl, 1.25 $NaH_2PO_4$, 2 $CaCl_2$, 1 $MgCl_2$, 1 kynurenic acid, 0.1 picrotoxin, bubbled with 5% $CO_2$/95% $O_2$. The slice recovery chamber can then returned to room temperature (20 to 22° C.) for recordings.

Neurons may be visualized using IR-DIC optics (Zeiss Axioskop 2 FS plus, Gottingen, Germany), and neurons from lamina I and the outer layer of lamina II can be selected based on their location relative to the substantia gelatinosa layer. Neurons can be patch-clamped using borosilicate glass patch pipettes with resistances of 3 to 6 MΩ. Current-clamp recordings of lamina I/II neurons in the intact slice, the external recording solution was the above Ringer solution, while the internal patch pipette solution contained (in mM): 140 KGluconate, 4 NaCl, 10 HEPES, 1 EGTA, 0.5 $MgCl_2$, 4 MgATP, 0.5 $Na_2GTP$, adjusted to pH 7.2 with 5 M KOH and to 290 mOsm with D-Mannitol (if necessary). Tonic firing neurons can be selected for current-clamp experiments, while phasic, delayed onset and single spike neurons may be discarded (22). Recordings can be digitized at 50 kHz and low-pass filtered at 2.4 kHz.

hERG $K^+$ Channel Activity

In addition to being able to modulate a particular voltage-gated ion channel, e.g. a sodium channel, it may be desirable that the compound has very low activity with respect to the hERG $K^+$ channel, which is expressed in the heart: compounds that block this channel with high potency may cause reactions which are fatal. See, e.g., Bowlby et al., "hERG ($KCNH_2$ or $K_v11.1$ $K^+$ Channels: Screening for Cardiac Arrhythmia Risk," *Curr. Drug Metab.* 9(9):965-70 (2008)). Thus, for a compound that modulates sodium channel activity, it may also be shown that the hERG $K^+$ channel is not inhibited or only minimally inhibited as compared to the inhibition of the primary channel targeted. Similarly, it may be desirable that the compound does not inhibit cytochrome p450, an enzyme that is required for drug detoxification. Such compounds may be particularly useful in the methods described herein.

Compounds can be tested using a standard electrophysiological assay (Kiss et al., *Assay & Drug Development Technologies*, 1:1-2, 2003; Bridgland-Taylor et al., *Journal of Pharmacological and Toxicological Methods*, 54:189-199, 2006). For example, compounds can be tested at 3 μM using IonWorks, and the percent inhibition of the peak of the slowly deactivating hERG tail current can be used to assess the affinity.

Pharmacokinetic Parameters

Preliminary exposure characteristics of the compounds can be evaluated using, e.g., an in vivo Rat Early Pharmacokinetic (EPK) study design to show bioavailability. For example, Male Sprague-Dawley rats can be dosed via oral (PO) gavage in a particular formulation. Blood samples can then be collected from the animals at 6 timepoints out to 4 hours post-dose. Pharmacokinetic analysis can then performed on the LC-MS/MS measured concentrations for each timepoint of each compound.

Pharmaceutical Compositions

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in *Remington: The Science and Practice of Pharmacy*, 21$^{st}$ Edition, Lippincott Williams & Wilkins, (2005); and

*Encyclopedia of Pharmaceutical Technology*, eds. J. Swarbrick and J. C. Boylan, 1988-1999, Marcel Dekker, New York, each of which is incorporated herein by reference.

The compounds described herein (e.g., a compound according to any of Formulas (I)-(X) or any of Compounds (1)-(92) of Table 1) may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, the compounds described herein (e.g., a compound according to any of Formulas (I)-(X) or any of Compounds (1)-(92) of Table 1) may be used alone, as mixtures of two or more compounds or in combination with other pharmaceuticals. An example of other pharmaceuticals to combine with the compounds described herein (e.g., a compound according to any of Formulas (I)-(X) or any of Compounds (1)-(92) of Table 1) would include pharmaceuticals for the treatment of the same indication. For example, in the treatment of pain, a compound may be combined with another pain relief treatment such as an NSAID, or a compound which selectively inhibits COX-2, or an opioid, or an adjuvant analgesic such as an antidepressant. Another example of a potential pharmaceutical to combine with the compounds described herein (e.g., a compound according to any of Formulas (I)-(X) or any of Compounds (1)-(92) of Table 1) would include pharmaceuticals for the treatment of different yet associated or related symptoms or indications. Depending on the mode of administration, the compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

The compounds of the invention may be prepared and used as pharmaceutical compositions comprising an effective amount of a compound described herein (e.g., a compound according to any of Formulas (I)-(X) or any of Compounds (1)-(92) of Table 1) and a pharmaceutically acceptable carrier or excipient, as is well known in the art. In some embodiments, the composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

For administration to animal or human subjects, the dosage of the compounds of the invention may be, for example, 0.01-50 mg/kg (e.g., 0.01-15 mg/kg or 0.1-10 mg/kg). For example, the dosage can be 10-30 mg/kg.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized for delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Formulations for oral use include tablets containing the active ingredient(s) in a mixture with nontoxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration may be indicated.

The following Examples are intended to illustrate the synthesis of a representative number of compounds and the use of these compounds for the modulation of sodium channel activity. Accordingly, the Examples are intended to illustrate, but not limit the invention. Additional compounds not specifically exemplified may be synthesized using conventional methods in combination with the methods described herein.

EXAMPLES

Example 1: Synthesis

Synthesis of (R)-2-amino-N—((S)-1-(3,5-bis(trifluoromethyl)phenoxy)propan-2-yl)-4-methylpentanamide

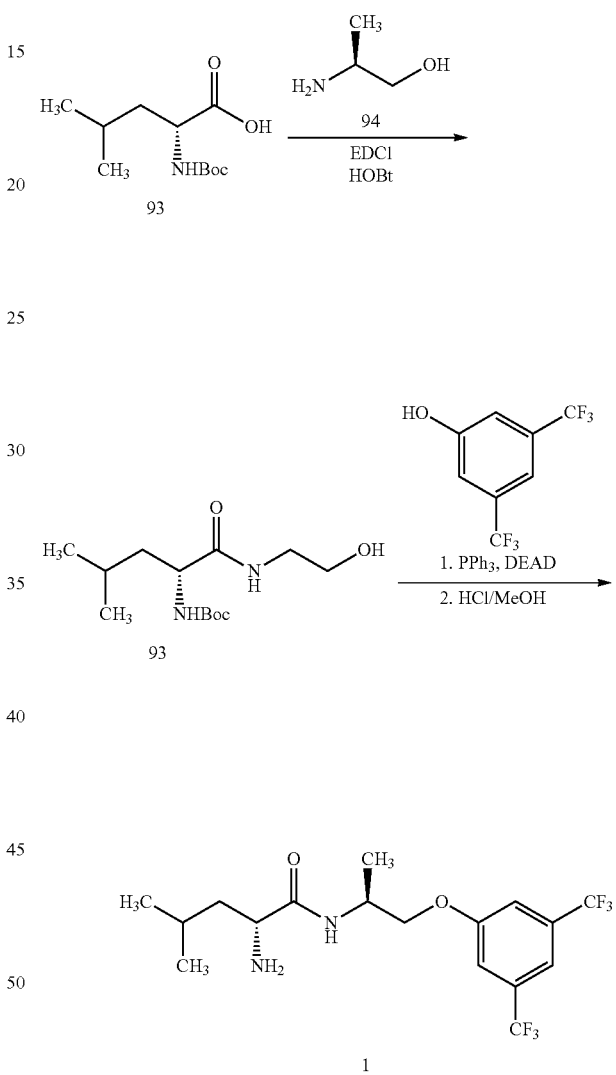

Standard conditions for amide bond formation can be used to prepare compounds described herein. For example, (R)-2-amino-N—((S)-1-(3,5-bis(trifluoromethyl)phenoxy)propan-2-yl)-4-methylpentanamide can be synthesized starting from commercially available (2R)-2-[(tert-butoxycarbonyl)amino]-4-methylpentanoic acid (Compound 93) and (R)-(−)-2-amino-1-propanol using standard 1-ethyl-3-(3-dimethylaminopropyl)carbodiimide (EDCl) and hydroxybenzotriazole (HOBt) amide coupling conditions to yield compounds of the invention (e.g., Compound 95 of Scheme 1). Subsequent Mitsunobu coupling with 3,5-bis(trifluoromethyl)phenol can afford Compound 1 of Table 1.

Synthesis of (2R)—N-(3,5-dimethyladamantan-1-yl)pyrrolidine-2-carboxamide

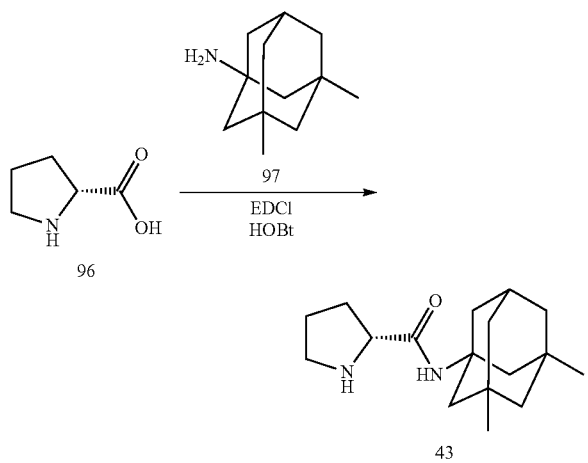

Scheme 2

(2R)—N-(3,5-dimethyladamantan-1-yl)pyrrolidine-2-carboxamide can be synthesized from D-proline and N-(3,5-dimethyl-1-adamantyl)-amine hydrochloride utilizing standard EDCI and HOBt amide coupling conditions as shown in Scheme 2.

Still other general procedures that can be used to obtain the compounds described herein are set forth in PCT/CA2012/000193, incorporated herein by reference.

Compounds of the invention include the following compounds listed in Table 1. Mass spectrometry can be employed with final compounds and at various stages throughout the synthesis as a confirmation of the identity of the product obtained (M+1). For the mass spectrometric analysis, samples can be prepared at an approximate concentration of 1 µg/mL in acetonitrile with 0.1% formic acid. Samples can be manually infused into an Applies Biosystems API3000 triple quadrupole mass spectrometer and scanned in Q1 in the range of 50 to 700 m/z.

TABLE 1

| No. | Structure | MW | Name |
|---|---|---|---|
| 1 | 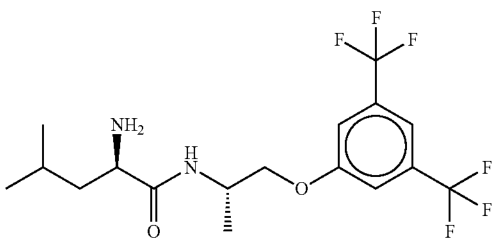 | 400.365 | (R)-2-amino-N-((S)-1-(3,5-bis(trifluoromethyl)phenoxy)propan-2-yl)-4-methylpentanamide |
| 2 | 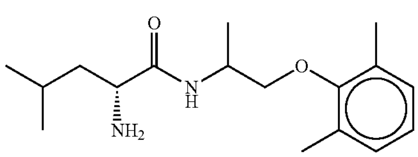 | 292.423 | (2R)-2-amino-N-(1-(2,6-dimethylphenoxy)propan-2-yl)-4-methylpentanamide |
| 3 | 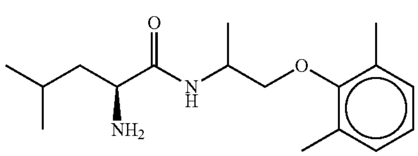 | 292.423 | (2S)-2-amino-N-(1-(2,6-dimethylphenoxy)propan-2-yl)-4-methylpentanamide |
| 4 | 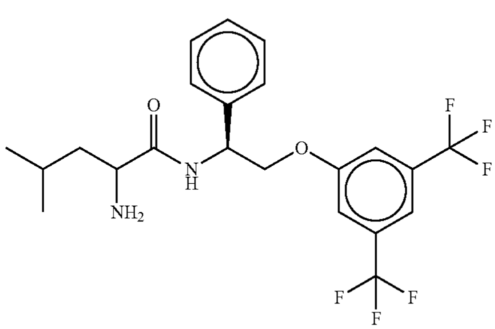 | 462.436 | 2-amino-N-((S)-2-(3,5-bis(trifluoromethyl)phenoxy)-1-phenylethyl)-4-methylpentanamide |

TABLE 1-continued

| No. | Structure | MW | Name |
|---|---|---|---|
| 5 | 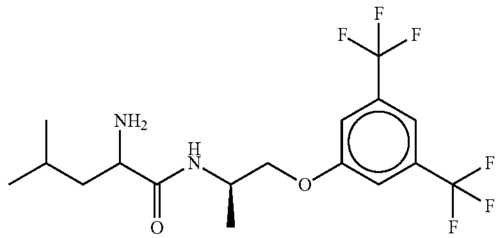 | 400.365 | 2-amino-N-((R)-1-(3,5-bis(trifluoromethyl)phenoxy)propan-2-yl)-4-methylpentanamide |
| 6 | 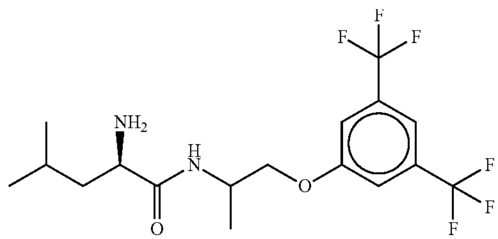 | 400.365 | (2R)-2-amino-N-(1-(3,5-bis(trifluoromethyl)phenoxy)propan-2-yl)-4-methylpentanamide |
| 7 | 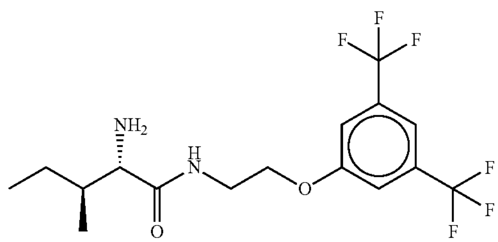 | 386.338 | (2S,3S)-2-amino-N-(2-(3,5-bis(trifluoromethyl)phenoxy)ethyl)-3-methylpentanamide |
| 8 | 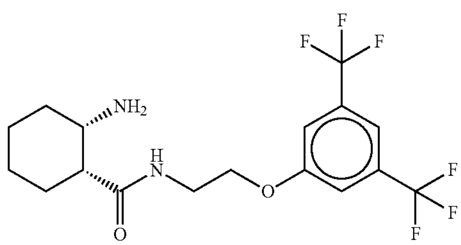 | 398.349 | (1R,2S)-2-amino-N-(2-(3,5-bis(trifluoromethyl)phenoxy)ethyl)cyclohexane-1-carboxamide |
| 9 | 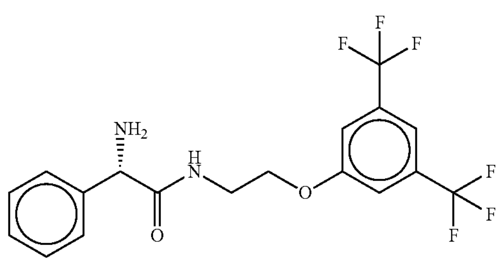 | 406.328 | (S)-2-amino-N-(2-(3,5-bis(trifluoromethyl)phenoxy)ethyl)-2-phenylacetamide |
| 10 | 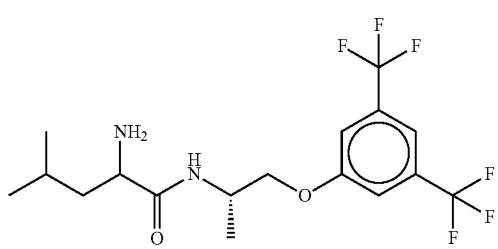 | 400.365 | 2-amino-N-((S)-1-(3,5-bis(trifluoromethyl)phenoxy)propan-2-yl)-4-methylpentanamide |

TABLE 1-continued

| No. | Structure | MW | Name |
|---|---|---|---|
| 11 | 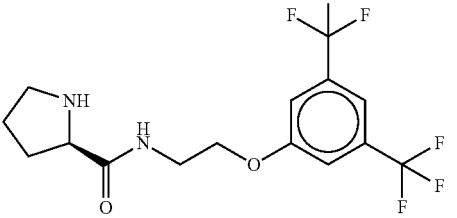 | 370.295 | (R)-N-(2-(3,5-bis(trifluoromethyl)phenoxy)ethyl)pyrrolidine-2-carboxamide |
| 12 | 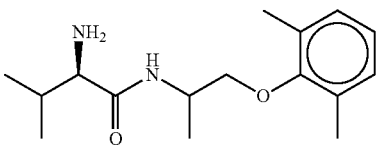 | 278.396 | (2R)-2-amino-N-(1-(2,6-dimethylphenoxy)propan-2-yl)-3-methylbutanamide |
| 13 | 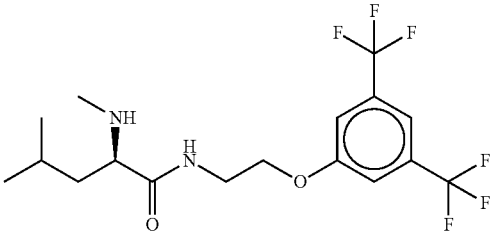 | 400.365 | (R)-N-(2-(3,5-bis(trifluoromethyl)phenoxy)ethyl)-4-methyl-2-(methylamino)pentanamide |
| 14 | 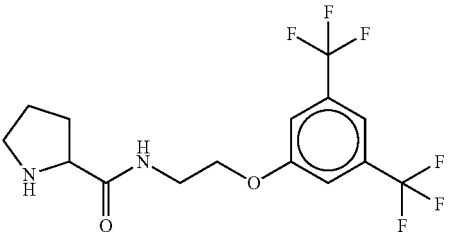 | 370.295 | N-(2-(3,5-bis(trifluoromethyl)phenoxy)ethyl)pyrrolidine-2-carboxamide |
| 15 | 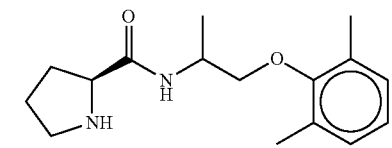 | 276.38 | (2S)-N-(1-(2,6-dimethylphenoxy)propan-2-yl)pyrrolidine-2-carboxamide |
| 16 | 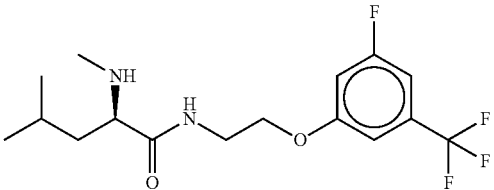 | 350.358 | (R)-N-(2-(3-fluoro-5-(trifluoromethyl)phenoxy)ethyl)-4-methyl-2-(methylamino)pentanamide |
| 17 | 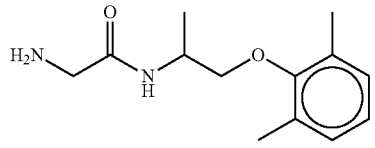 | 236.315 | 2-amino-N-(1-(2,6-dimethylphenoxy)propan-2-yl)acetamide |
| 18 | 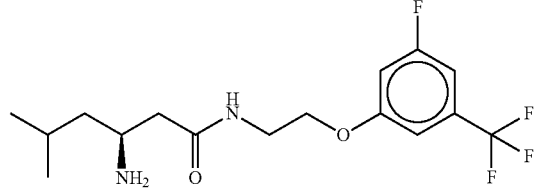 | 350.358 | (S)-3-amino-N-(2-(3-fluoro-5-(trifluoromethyl)phenoxy)ethyl)-5-methylhexanamide |

TABLE 1-continued

| No. | Structure | MW | Name |
|---|---|---|---|
| 19 | 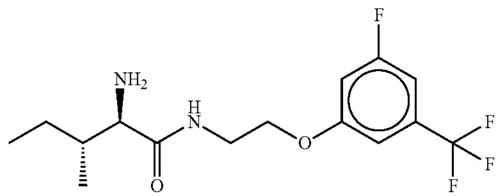 | 336.331 | (2R,3R)-2-amino-N-(2-(3-fluoro-5-(trifluoromethyl)phenoxy)ethyl)-3-methylpentanamide |
| 20 | 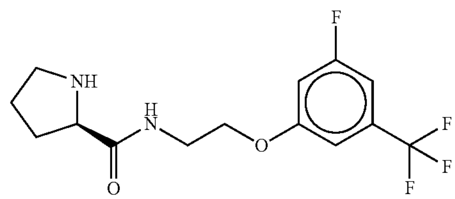 | 320.288 | (R)-N-(2-(3-fluoro-5-(trifluoromethyl)phenoxy)ethyl) pyrrolidine-2-carboxamide |
| 21 | 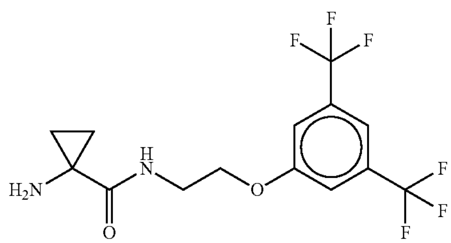 | 356.268 | 1-amino-N-(2-(3,5-bis(trifluoromethyl)phenoxy)ethyl) cyclopropane-1-carboxamide |
| 22 | 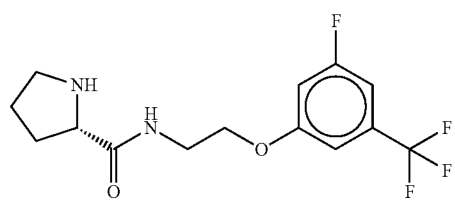 | 320.288 | (S)-N-(2-(3-fluoro-5-(trifluoromethyl)phenoxy)ethyl) pyrrolidine-2-carboxamide |
| 23 | 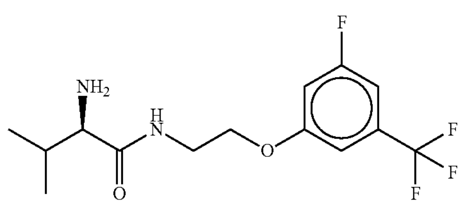 | 322.304 | (R)-2-amino-N-(2-(3-fluoro-5-(trifluoromethyl)phenoxy)ethyl)-3-methylbutanamide |
| 24 | 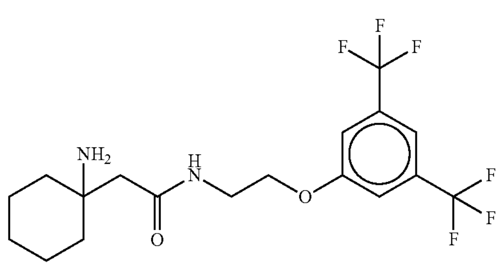 | 412.376 | 2-(1-aminocyclohexyl)-N-(2-(3,5-bis(trifluoromethyl)phenoxy)ethyl) acetamide |

TABLE 1-continued

| No. | Structure | MW | Name |
|---|---|---|---|
| 25 | 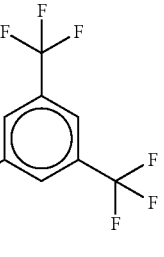 | 400.321 | (R)-N-(3-(3,5-bis(trifluoromethyl)phenoxy)propyl)morpholine-2-carboxamide |
| 26 | 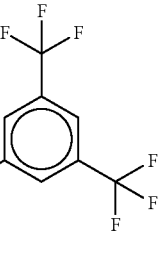 | 398.349 | (S)-N-(3-(3,5-bis(trifluoromethyl)phenoxy)propyl)piperidine-2-carboxamide |
| 27 | 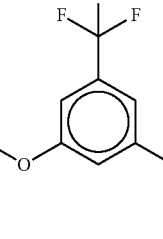 | 452.373 | (S)-2-amino-N-(3-(3,5-bis(trifluoromethyl)phenoxy)propyl)-3-(3-fluorophenyl)propanamide |
| 28 | 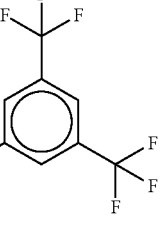 | 412.376 | N-(3-(3,5-bis(trifluoromethyl)phenoxy)propyl)-2-methylpiperidine-2-carboxamide |
| 29 | 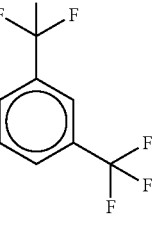 | 384.322 | (R)-N-(3-(3,5-bis(trifluoromethyl)phenoxy)propyl)pyrrolidine-2-carboxamide |
| 30 | 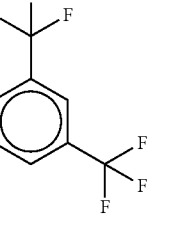 | 358.284 | (S)-2-amino-N-(3-(3,5-bis(trifluoromethyl)phenoxy)propyl)propanamide |

TABLE 1-continued

| No. | Structure | MW | Name |
|---|---|---|---|
| 31 | 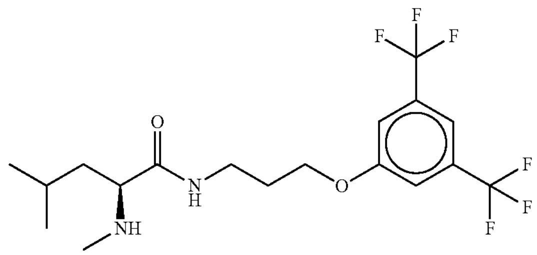 | 414.392 | (S)-N-(3-(3,5-bis(trifluoromethyl)phenoxy)propyl)-4-methyl-2-(methylamino)pentanamide |
| 32 | 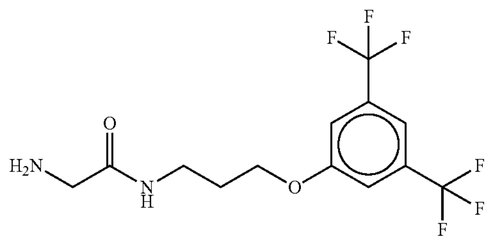 | 344.257 | 2-amino-N-(3-(3,5-bis(trifluoromethyl)phenoxy)propyl)acetamide |
| 33 | 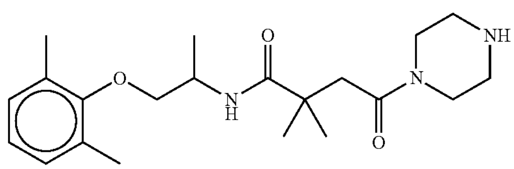 | 375.513 | N-(1-(2,6-dimethylphenoxy)propan-2-yl)-2,2-dimethyl-4-oxo-4-(piperazin-1-yl)butanamide |
| 34 | 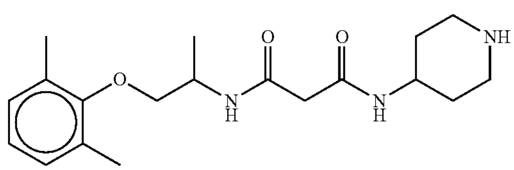 | 347.459 | N1-(1-(2,6-dimethylphenoxy)propan-2-yl)-N3-(piperidin-4-yl)malonamide |
| 35 | 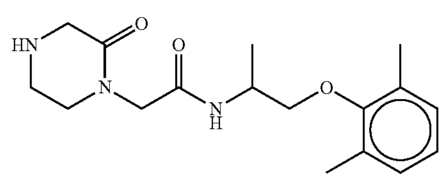 | 319.405 | N-(1-(2,6-dimethylphenoxy)propan-2-yl)-2-(2-oxopiperazin-1-yl)acetamide |
| 36 | 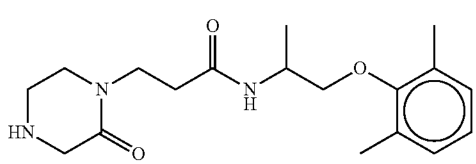 | 333.432 | N-(1-(2,6-dimethylphenoxy)propan-2-yl)-3-(2-oxopiperazin-1-yl)propanamide |
| 37 | 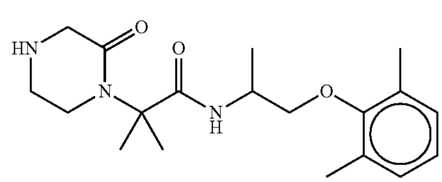 | 347.459 | N-(1-(2,6-dimethylphenoxy)propan-2-yl)-2-methyl-2-(2-oxopiperazin-1-yl)propanamide |

TABLE 1-continued

| No. | Structure | MW | Name |
|---|---|---|---|
| 38 | 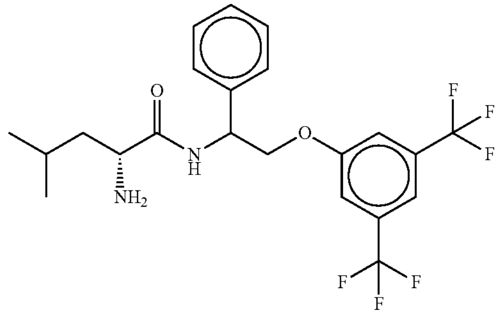 | 462.436 | (2R)-2-amino-N-(2-(3,5-bis(trifluoromethyl)phenoxy)-1-phenylethyl)-4-methylpentanamide |
| 39 | 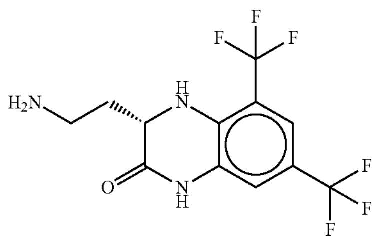 | 327.23 | (S)-3-(2-aminoethyl)-5,7-bis(trifluoromethyl)-3,4-dihydroquinoxalin-2(1H)-one |
| 40 | 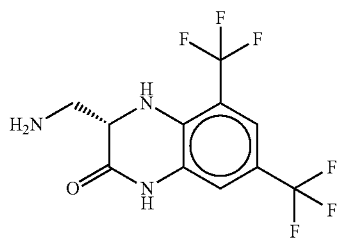 | 313.203 | (S)-3-(aminomethyl)-5,7-bis(trifluoromethyl)-3,4-dihydroquinoxalin-2(1H)-one |
| 41 | 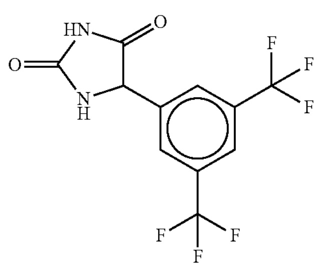 | 312.171 | 5-(3,5-bis(trifluoromethyl)phenyl)imidazolidine-2,4-dione |
| 42 | 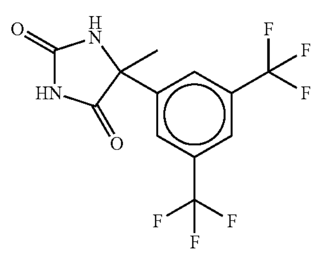 | 326.198 | 5-(3,5-bis(trifluoromethyl)phenyl)-5-methylimidazolidine-2,4-dione |
| 43 | 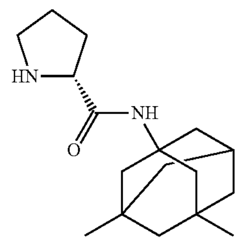 [SMILES: CC12CC3CC(C)(C1)CC(NC(=O)[C@H]1CCCN1)(C3)C2] | 276.424 | (2R)-N-(3,5-dimethyladamantan-1-yl)pyrrolidine-2-carboxamide |

TABLE 1-continued

| No. | Structure | MW | Name |
|---|---|---|---|
| 44 | 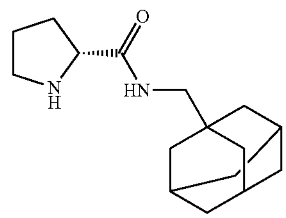 [SMILES: O=C(NCC12CC3CC(CC(C3)C1)C2)[C@H]1CCCN1] | 262.397 | (R)-N-(adamantan-1-ylmethyl)pyrrolidine-2-carboxamide |
| 45 | 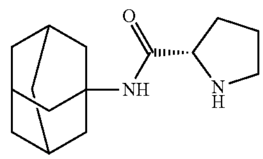 [SMILES: O=C(NC12CC3CC(CC(C3)C1)C2)[C@@H]1CCCN1] | 248.37 | (S)-N-(adamantan-1-yl)pyrrolidine-2-carboxamide |
| 46 | 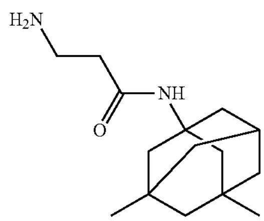 [SMILES: CC12CC3CC(C)(C1)CC(NC(=O)CCN)(C3)C2] | 250.386 | 3-amino-N-(3,5-dimethyladamantan-1-yl)propanamide |
| 47 | 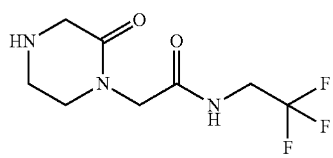 [SMILES: O=C(CN1CCNCC1=O)NCC(F)(F)F] | 239.198 | 2-(2-oxopiperazin-1-yl)-N-(2,2,2-trifluoroethyl)acetamide |
| 48 | 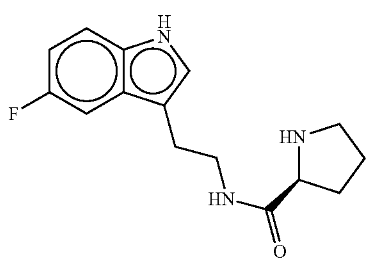 | 275.327 | (S)-N-(2-(5-fluoro-1H-indol-3-yl)ethyl)pyrrolidine-2-carboxamide |
| 49 | 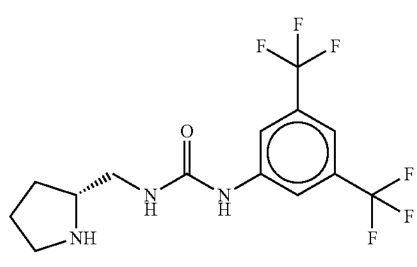 | 355.284 | (R)-1-(3,5-bis(trifluoromethyl)phenyl)-3-(pyrrolidin-2-ylmethyl)urea |
| 50 | 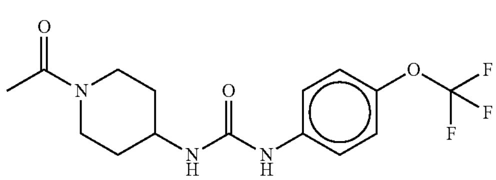 | 345.322 | 1-(1-acetylpiperidin-4-yl)-3-(4-(trifluoromethoxy)phenyl)urea |

TABLE 1-continued

| No. | Structure | MW | Name |
|---|---|---|---|
| 51 | 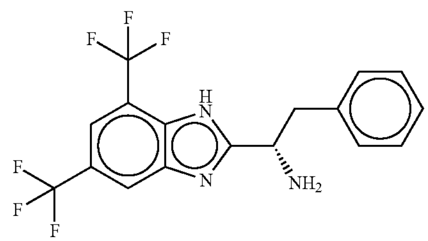 | 373.302 | (S)-1-(4,6-bis(trifluoromethyl)-1H-benzo[d]imidazol-2-yl)-2-phenylethan-1-amine |
| 52 | 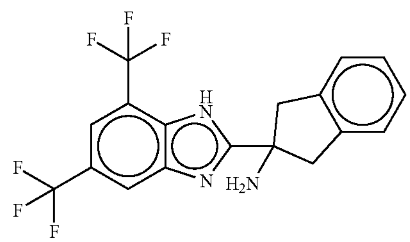 | 385.313 | 2-(4,6-bis(trifluoromethyl)-1H-benzo[d]imidazol-2-yl)-2,3-dihydro-1H-inden-2-amine |
| 53 | 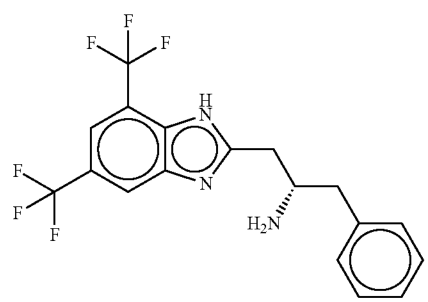 | 387.329 | (S)-1-(4,6-bis(trifluoromethyl)-1H-benzo[d]imidazol-2-yl)-3-phenylpropan-2-amine |
| 54 | 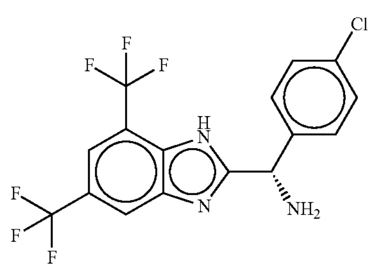 | 393.717 | (S)-(4,6-bis(trifluoromethyl)-1H-benzo[d]imidazol-2-yl)(4-chlorophenyl)methanamine |
| 55 | 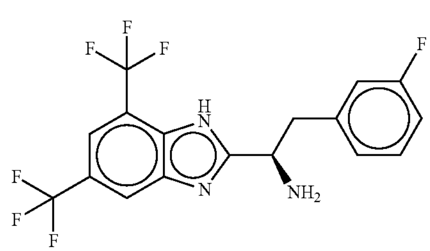 | 391.293 | (R)-1-(4,6-bis(trifluoromethyl)-1H-benzo[d]imidazol-2-yl)-2-(3-fluorophenyl)ethan-1-amine |

TABLE 1-continued

| No. | Structure | MW | Name |
|---|---|---|---|
| 56 | 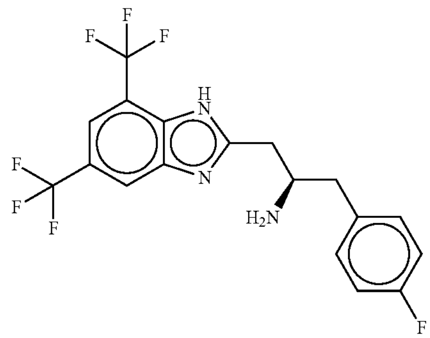 | 405.32 | (R)-1-(4,6-bis(trifluoromethyl)-1H-benzo[d]imidazol-2-yl)-3-(4-fluorophenyl)propan-2-amine |
| 57 | 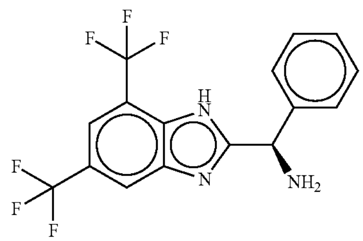 | 359.275 | (R)-(4,6-bis(trifluoromethyl)-1H-benzo[d]imidazol-2-yl)(phenyl)methanamine |
| 58 | 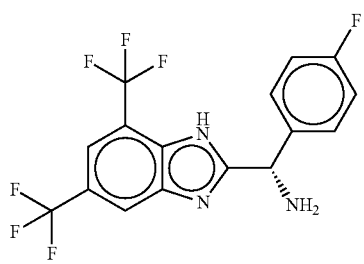 | 377.266 | (S)-(4,6-bis(trifluoromethyl)-1H-benzo[d]imidazol-2-yl)(4-fluorophenyl)methanamine |
| 59 | 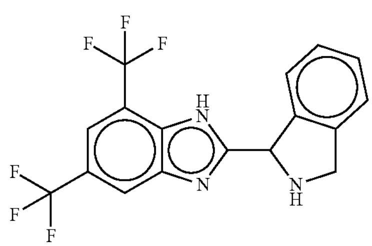 | 371.286 | 2-(isoindolin-1-yl)-4,6-bis(trifluoromethyl)-1H-benzo[d]imidazole |
| 60 | 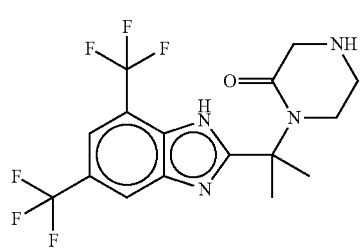 | 394.321 | 1-(2-(4,6-bis(trifluoromethyl)-1H-benzo[d]imidazol-2-yl)propan-2-yl)piperazin-2-one |

TABLE 1-continued

| No. | Structure | MW | Name |
|---|---|---|---|
| 61 | 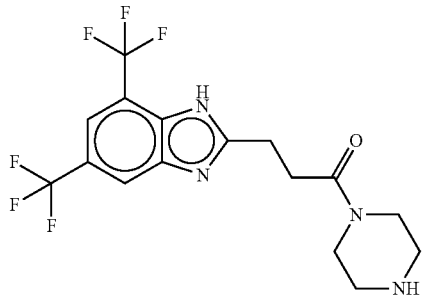 | 394.321 | 3-(4,6-bis(trifluoromethyl)-1H-benzo[d]imidazol-2-yl)-1-(piperazin-1-yl)propan-1-one |
| 62 | 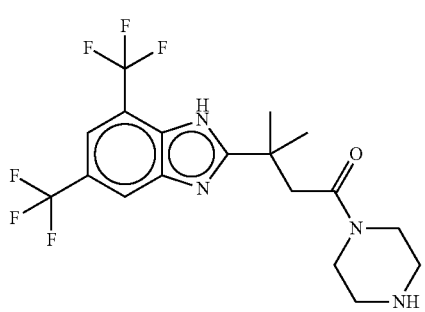 | 422.375 | 3-(4,6-bis(trifluoromethyl)-1H-benzo[d]imidazol-2-yl)-3-methyl-1-(piperazin-1-yl)butan-1-one |
| 63 | 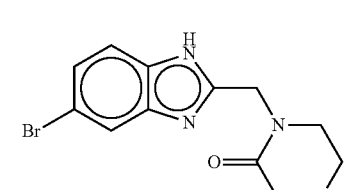 | 309.167 | 1-((6-bromo-1H-benzo[d]imidazol-2-yl)methyl)piperazin-2-one |
| 64 | 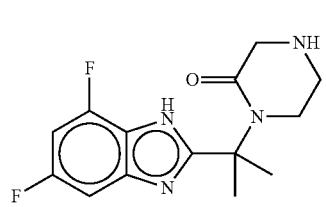 | 294.306 | 1-(2-(4,6-difluoro-1H-benzo[d]imidazol-2-yl)propan-2-yl)piperazin-2-one |
| 65 | 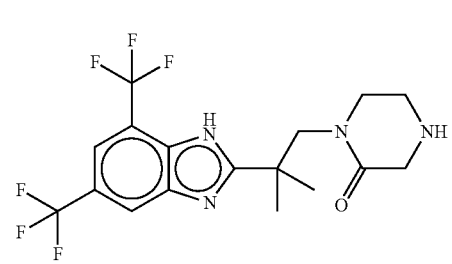 | 408.348 | 1-(2-(4,6-bis(trifluoromethyl)-1H-benzo[d]imidazol-2-yl)-2-methylpropyl)piperazin-2-one |
| 66 | 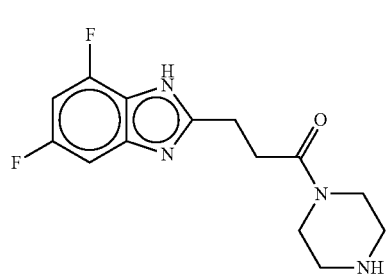 | 294.306 | 3-(4,6-difluoro-1H-benzo[d]imidazol-2-yl)-1-(piperazin-1-yl)propan-1-one |

TABLE 1-continued

| No. | Structure | MW | Name |
|---|---|---|---|
| 67 | 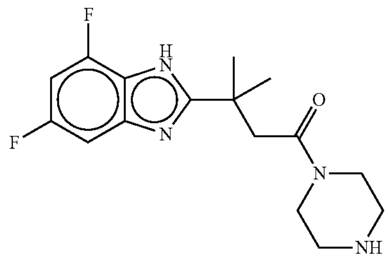 | 322.36 | 3-(4,6-difluoro-1H-benzo[d]imidazol-2-yl)-3-methyl-1-(piperazin-1-yl)butan-1-one |
| 68 | 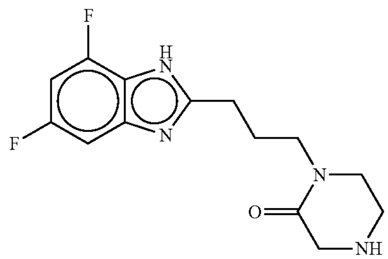 | 294.306 | 1-(3-(4,6-difluoro-1H-benzo[d]imidazol-2-yl)propyl)piperazin-2-one |
| 69 | 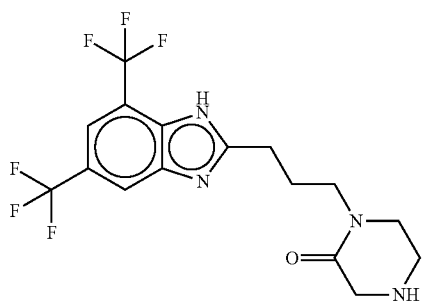 | 394.321 | 1-(3-(4,6-bis(trifluoromethyl)-1H-benzo[d]imidazol-2-yl)propyl)piperazin-2-one |
| 70 | 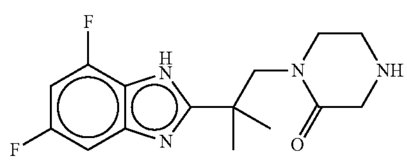 | 308.333 | 1-(2-(4,6-difluoro-1H-benzo[d]imidazol-2-yl)-2-methylpropyl)piperazin-2-one |
| 71 | 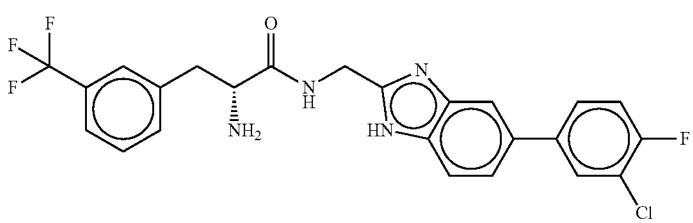 | 490.887 | (R)-2-amino-N-((6-(3-chloro-4-fluorophenyl)-1H-benzo[d]imidazol-2-yl)methyl)-3-(3-(trifluoromethyl)phenyl)propanamide |
| 72 | 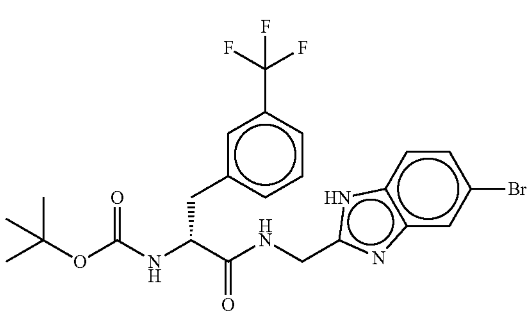 | 541.369 | tert-butyl (R)-(1-(((6-bromo-1H-benzo[d]imidazol-2-yl)methyl)amino)-1-oxo-3-(3-(trifluoromethyl)phenyl)propan-2-yl)carbamate |

TABLE 1-continued

| No. | Structure | MW | Name |
|---|---|---|---|
| 73 | 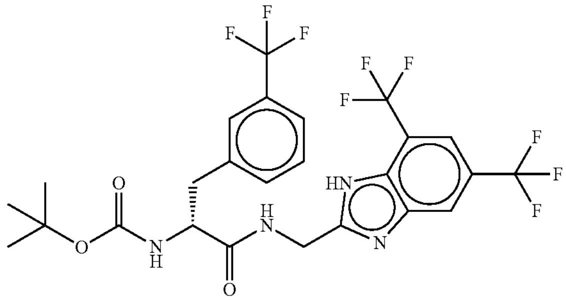 | 598.47 | tert-butyl (R)-(1-(((4,6-bis(trifluoromethyl)-1H-benzo[d]imidazol-2-yl)methyl)amino)-1-oxo-3-(3-(trifluoromethyl)phenyl)propan-2-yl)carbamate |
| 74 | 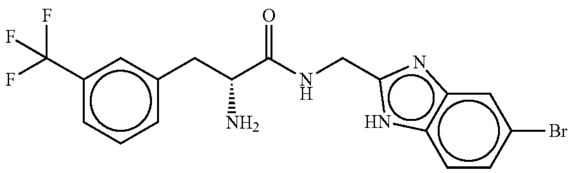 | 441.252 | (R)-2-amino-N-((6-bromo-1H-benzo[d]imidazol-2-yl)methyl)-3-(3-(trifluoromethyl)phenyl)propanamide |
| 75 | 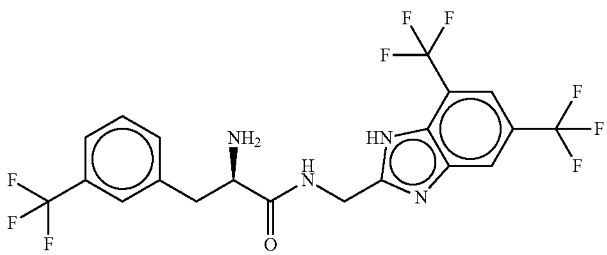 | 498.353 | (R)-2-amino-N-((4,6-bis(trifluoromethyl)-1H-benzo[d]imidazol-2-yl)methyl)-3-(3-(trifluoromethyl)phenyl)propanamide |
| 76 | 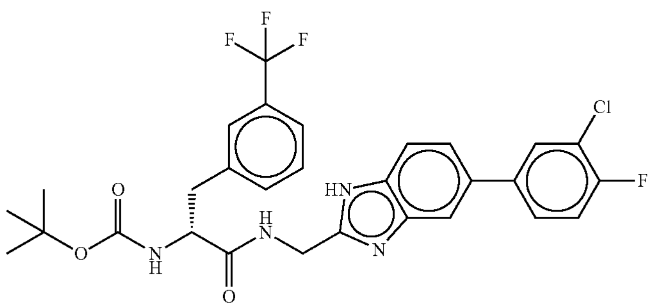 | 591.004 | tert-butyl (R)-(1-(((6-(3-chloro-4-fluorophenyl)-1H-benzo[d]imidazol-2-yl)methyl)amino)-1-oxo-3-(3-(trifluoromethyl)phenyl)propan-2-yl)carbamate |
| 77 | 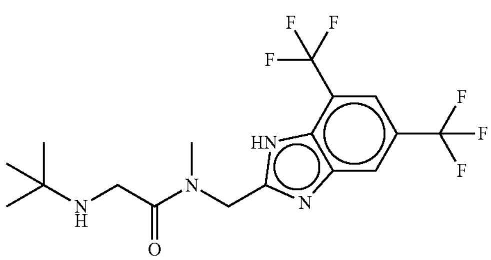 | 410.364 | N-((4,6-bis(trifluoromethyl)-1H-benzo[d]imidazol-2-yl)methyl)-2-(tert-butylamino)-N-methylacetamide |
| 78 | 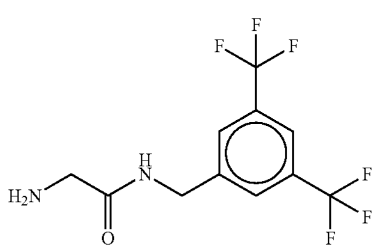 | 300.204 | 2-amino-N-(3,5-bis(trifluoromethyl)benzyl)acetamide |

TABLE 1-continued

| No. | Structure | MW | Name |
|---|---|---|---|
| 79 | 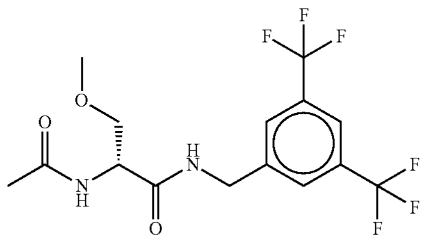 | 386.294 | (R)-2-acetamido-N-(3,5-bis(trifluoromethyl)benzyl)-3-methoxypropanamide |
| 80 | 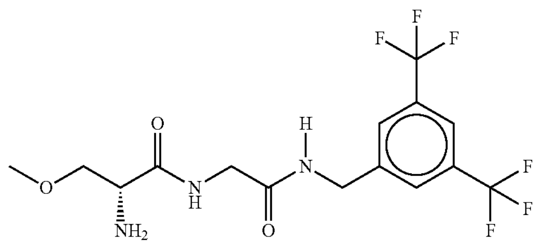 | 401.309 | (R)-2-amino-N-(2-((3,5-bis(trifluoromethyl)benzyl)amino)-2-oxoethyl)-3-methoxypropanamide |
| 81 | 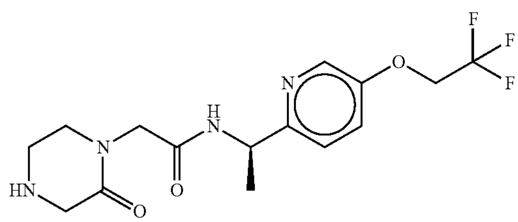 | 360.337 | (R)-2-(2-oxopiperazin-1-yl)-N-(1-(5-(2,2,2-trifluoroethoxy)pyridin-2-yl)ethyl)acetamide |
| 82 | 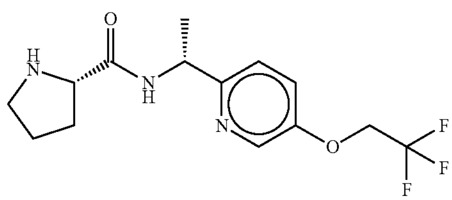 | 317.312 | (S)-N-((R)-1-(5-(2,2,2-trifluoroethoxy)pyridin-2-yl)ethyl)pyrrolidine-2-carboxamide |
| 83 | 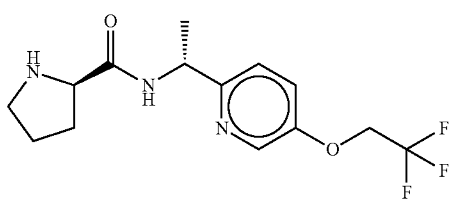 | 317.312 | (R)-N-((R)-1-(5-(2,2,2-trifluoroethoxy)pyridin-2-yl)ethyl)pyrrolidine-2-carboxamide |
| 84 | 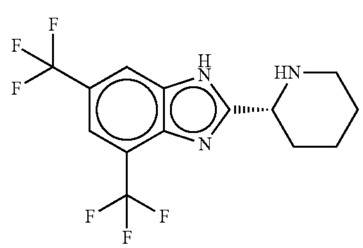 | 337.269 | (R)-2-(piperidin-2-yl)-5,7-bis(trifluoromethyl)-1H-benzo[d]imidazole |
| 85 | 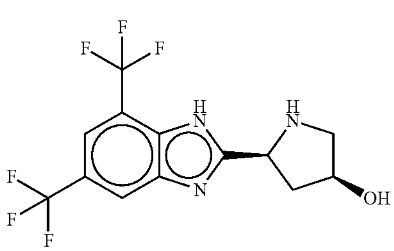 | 339.241 | (3S,5S)-5-(5,7-bis(trifluoromethyl)-1H-benzo[d]imidazol-2-yl)pyrrolidin-3-ol |

TABLE 1-continued

| No. | Structure | MW | Name |
|---|---|---|---|
| 86 | 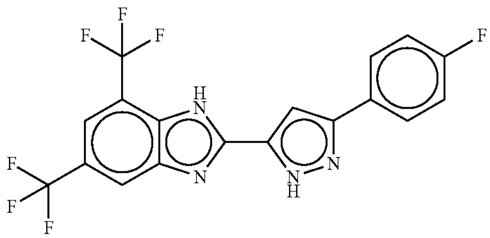 | 414.287 | 2-(5-(4-fluorophenyl)-1H-pyrazol-3-yl)-4,6-bis(trifluoromethyl)-1H-benzo[d]imidazole |
| 87 | 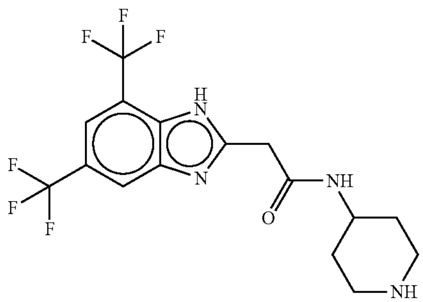 | 394.321 | 2-(4,6-bis(trifluoromethyl)-1H-benzo[d]imidazol-2-yl)-N-(piperidin-4-yl)acetamide |
| 88 | 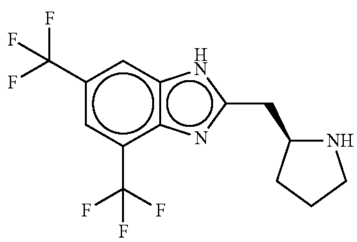 | 337.269 | (S)-2-(pyrrolidin-2-ylmethyl)-4,6-bis(trifluoromethyl)-1H-benzo[d]imidazole |
| 89 | 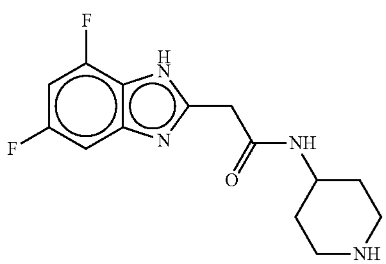 | 294.306 | 2-(4,6-difluoro-1H-benzo[d]imidazol-2-yl)-N-(piperidin-4-yl)acetamide |
| 90 | 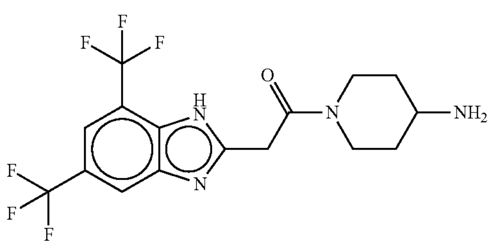 | 394.321 | 1-(4-aminopiperidin-1-yl)-2-(4,6-bis(trifluoromethyl)-1H-benzo[d]imidazol-2-yl)ethan-1-one |
| 91 | 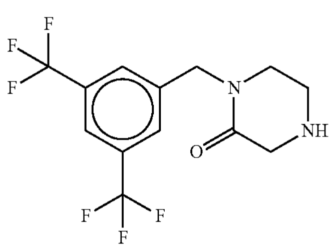 | 326.242 | 1-(3,5-bis(trifluoromethyl)benzyl)piperazin-2-one |

TABLE 1-continued

| No. | Structure | MW | Name |
|---|---|---|---|
| 92 | 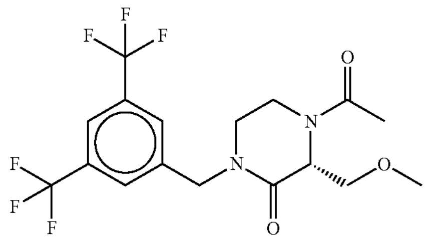 | 412.332 | (R)-4-acetyl-1-(3,5-bis(trifluoromethyl)benzyl)-3-(methoxymethyl)piperazin-2-one |

Example 2: Ion Channel Activity Assays

The compounds described herein were assayed for the ability to block Nav1.7. These compounds can also be assayed for modulation of, e.g., voltage gated sodium channels (e.g., other Na⁺ channel isoforms or Ca²⁺ channels such as $Ca_V3.2$ T-type channels). Exemplary methods are described herein, but additional methods are known in the art.

Cell Generation and Maintenance

The generation of a HEK 293F cell line stably expressing human Nav1.7/Navβ1 was achieved by co-transfecting human SCN9A and human SCN1B cDNAs, subcloned into plasmid vectors, utilizing standard transfection techniques. Clones were selected using appropriate selection agents (0.3 mg/mL Zeocin and 0.8 mg/mL Geneticin) and maintained in Dulbecco's Modified Eagle medium, 10% fetal bovine serum, 1% non-essential amino acids to ~80% confluence at 37° C. in a humidified incubator with 95% atmosphere and 5% $CO_2$.

Nav1.5 Assay

Inhibition of the TTX-resistant Nav1.5 sodium channel, a key cardiac ion channel, can have profound effects on the duration and amplitude of the cardiac action potential and can result in arrhythmias and other heart malfunctions. To assess the potential cardiac liability of compounds at an early stage in the drug discovery process, a Nav1.5 sodium channel screening assay can be performed on Molecular Device's PatchXpress™ automated electrophysiology platform. Under voltage-clamp conditions, Nav1.5 currents can be recorded from HEK cells expressing the human Nav1.5 channel in the absence and presence of increasing concentrations of the test compound to obtain an $IC_{50}$ value. The external recording solution can contain (in mM): 90 TEACl, 50 NaCl, 1.8 CaCl, 1 $MgCl_2$, 10 HEPES, 10 glucose, adjusted to pH 7.4 with TEA-OH and to 300 mOsm with sucrose (if necessary), while the internal patch pipette solution contained (in mM): 129 CsF, 2 $MgCl_2$, 11 EGTA, 10 HEPES, 3 $Na_2ATP$ adjusted to pH 7.2 with CsOH and to 290 mOsm with sucrose (if necessary). Nav1.5 channel currents can be evoked using a cardiac action potential waveform at 1 Hz, digitized at 31.25 kHz and low-pass filtered at 12 kHz.

Assessment of Nav1.7 Activity

On the day of each experiment, cells that were grown to 80% confluence in a T75 flask were harvested for use on PatchXpress (Molecular Devices, CA, USA). Following a recovery period at 37° C. in a humidified incubator with 95% atmosphere and 5% $CO_2$ in Dulbecco's Modified Eagle Medium, the media was replaced with an external recording solution containing (in mM): 90 TEACl, 50 NaCl, 1.8 $CaCl_2$, 1 $MgCl_2$, 10 HEPES, 10 glucose, adjusted to pH 7.4 with TEAOH and 300 mOsm with sucrose. The internal recording solution contained (in mM): 129 CsF, 2 $MgCl_2$, 11 EGTA, 10 HEPES, 6 NaCl, 3 $Na_2ATP$ adjusted to pH 7.2 with CsOH and 280 mOsm with sucrose. The automated liquid handling facility of PatchXpress dispensed cells and added compound. Modulation of Nav1.7 channels by compounds was assessed by promoting the channels into the inactivated state using a conditioning voltage pulse of variable amplitude, followed by a brief hyperpolarizing pulse with a subsequent depolarized voltage step to measure the current amplitude in the presence and absence of compound. Compounds were assayed at 10 µM. Based upon this Patch express protocol, four electrophysiological parameters were measured relative to a 0.2% DMSO vehicle control (Table 2). This first data column describes compound induced shifts in the voltage dependence of slow inactivation (Table 2: hNav1.7: Reduction in current at 20 mV) at which ~50% of the channels were inactivated. The second data column describes the change in the population of Nav1.7 channels undergoing fast inactivation before and after a 30 sec conditioning voltage pulse at 20 mV (Table 2: hNav1.7: Reduction in current at 20 mV (normalized data). The ratio of these currents elicited by a hyperpolarizing pulse before and after preconditioning allows the determination of the fraction of Nav1.7 channels in the slow inactivated state. The third data column displays the voltage dependence of activation (Table 2: hNav1.7: Voltage dependence of activation). Lastly, the fourth data column describes the voltage dependence of fast inactivation in which ~50% of the channels were inactivated (Table 2: hNav1.7: Voltage dependence of fast inactivation).

In some cases, the potency of compounds was measured using either the Patchliner automated patch clamp platform (Nanion) or manual patch clamp techniques. Both approaches allowed the compounds to be characterized based upon the ability of a compound to modulate use- and/or state-dependence. The potency data is tabulated in Table 3 and is represented by eight data fields. The first four fields represent potency data measured with the Patchliner automated platform under varying use- and state-dependent electrophysiology protocols similar to the Patch express protocols detailed above. The first data column describes the potency of compounds when the Nav1.7 channel is being repetitively activated at a 7 Hz hyperpolarization frequency (Table 3: hNav1.7: IC50 of inward current block at 7 Hz, Automated patchclamp). The second data column represents the potency at which 50% of the initial hyperpolarization pulse is inhibited by the compounds (Table 3: hNav1.7: IC50 of P1 block, Automated patchclamp). The third data column details the potency of compounds in their ability to block 50% of Nav1.7 channels when these channels are induced into the slow inactivated state (Table 3: hNav1.7: IC50 of slow inactivation block, Automated patchclamp). The fourth data column shows potency data at which 50% of channel activity is blocked when repetitively activated at a 0.25 Hz hyperpolarizing frequency (Table 3: hNav1.7: IC50 of inward current block at 0.25 Hz, Automated patchclamp). The next three data fields describe the data generated from manual patchclamp electrophysiology measurements using similar methods to those employed for automated patch-clamp studies. The fifth and sixth data columns demonstrate the potency at which 50% of channel activity was inhibited when repetitively activated with a 7 Hz or 0.25 Hz hyper-polarization frequency, respectively (Table 3: hNav1.7: IC50 of inward current block at 7 Hz, Manual patchclamp) (hNav1.7: IC50 of inward current block at 0.25 Hz, Manual patchlamp). The seventh column shows the potency of certain compounds which block 50% channel activity when the Nav1.7 channel is in the slow inactivated state (hNav1.7: IC50 of slow inactivation block, Manual patchclamp). The last column characterizes the state-dependence of compound inhibition. Compounds that maintain the greatest potency for the slow inactivated state over fast inactivated or tonic inhibition at 0.25 Hz are characterized as "state dependent, blocker of slow inactivation".

TABLE 2

| Compound # | hNav1.7: Shift in voltage dependence of inactivation (mV) Delta Vhalf | hNav1.7: Reduction in current at 20 mV (normalized data) Delta Ratio | hNav1.7: Voltage dependence of activation (mV) VDEP | hNav1.7: Voltage dependence of fast inactivation (mV) VDEP |
|---|---|---|---|---|
| 1 | −20.90 | −0.30 | −8.60 | −6.80 |
| 2 | −32.20 | −0.29 | −10.00 | −8.20 |
| 3 | −28.00 | −0.28 | −8.10 | −7.40 |
| 4 | −31.10 | −0.27 | −5.80 | −11.50 |
| 5 | −25.20 | −0.26 | −4.60 | −6.30 |
| 6 | −32.70 | −0.25 | −4.80 | −6.20 |
| 7 | −21.40 | −0.24 | −8.10 | −6.60 |
| 8 | −16.40 | −0.23 | −7.80 | −6.80 |
| 9 | −18.30 | −0.21 | −8.10 | −7.90 |
| 10 | −31.40 | −0.20 | −3.70 | −3.50 |
| 11 | −19.70 | −0.20 | −5.00 | −3.90 |
| 12 | −25.70 | −0.19 | −7.30 | −4.30 |
| 13 | −23.80 | −0.17 | −5.90 | −4.00 |
| 14 | −25.30 | −0.17 | −4.00 | −1.10 |
| 15 | −20.60 | −0.16 | −6.00 | −4.90 |
| 43 | −8.50 | −0.12 | −11.40 | −5.70 |
| 16 | −14.70 | −0.11 | −2.80 | −2.60 |
| 44 | −5.40 | −0.11 | −13.20 | −6.00 |
| 17 | −12.40 | −0.10 | −5.80 | −5.90 |
| 18 | −11.90 | −0.09 | −2.60 | −3.90 |
| 39 | −4.90 | −0.08 | −7.40 | −3.10 |
| 19 | −10.00 | −0.08 | −8.00 | −3.50 |
| 45 | −6.20 | −0.07 | −5.10 | −7.00 |
| 46 | −1.70 | −0.04 | −7.90 | −4.50 |
| 40 | −3.90 | −0.02 | −6.60 | −2.60 |
| 47 | −2.50 | −0.02 | −8.90 | −4.40 |
| 48 | −1.80 | −0.01 | −4.80 | −3.00 |
| 20 | −7.20 | −0.01 | −6.80 | −4.40 |
| 21 | −4.20 | 0.00 | −5.20 | −10.40 |
| 22 | −7.00 | 0.06 | −6.50 | −1.80 |
| 33 | −5.30 | −0.07 | −8.70 | −6.00 |
| 34 | −2.30 | −0.03 | −6.30 | −5.10 |
| 41 | −2.80 | 0.00 | −9.00 | −5.30 |
| 42 | 0.50 | 0.02 | −6.60 | −2.50 |
| 49 | −6.40 | −0.18 | −10.20 | −7.80 |
| 50 | −0.30 | 0.02 | −8.30 | −2.10 |
| 37 | −5.00 | −0.09 | −9.00 | −6.30 |
| 35 | −3.00 | −0.06 | −7.40 | −4.40 |
| 36 | −2.90 | −0.04 | −12.90 | −5.00 |
| 38 | −33.7 | −0.34 | −11.5 | −15.3 |
| 51 | −20.8 | −0.35 | −9.5 | −11.5 |
| 52 | −14.9 | −0.28 | −7.2 | −8.2 |
| 53 | −7.2 | −0.28 | −8.2 | −3.9 |
| 54 | −27.4 | −0.26 | −10 | −8.6 |
| 55 | −15.1 | −0.26 | −8.6 | −6.2 |
| 56 | −16.8 | −0.21 | −14.4 | −3.3 |
| 57 | −10.4 | −0.21 | −4.7 | −4.8 |
| 58 | −8.6 | −0.21 | −4 | −4.9 |
| 59 | −12.8 | −0.2 | −9 | −5.9 |
| 60 | −9.2 | −0.19 | −8.3 | −3.8 |
| 61 | −9.2 | −0.19 | −11.3 | −5.1 |
| 62 | −12.5 | −0.19 | −7.4 | −3.8 |
| 63 | −9.7 | −0.17 | −8.1 | −6.4 |
| 64 | −5.4 | −0.16 | −7.1 | −5.9 |
| 65 | −3.5 | −0.16 | −8.1 | −6.2 |
| 66 | −12.0 | −0.14 | −14.5 | −6.9 |
| 67 | −7.8 | −0.13 | −9.7 | −7.6 |
| 68 | −11.4 | −0.1 | −11.6 | −4.9 |
| 69 | −7.5 | −0.09 | −9.2 | −4.9 |
| 70 | −4.6 | −0.08 | −5.3 | −5.7 |

TABLE 2-continued

| Compound # | hNav1.7: Shift in voltage dependence of inactivation (mV) Delta Vhalf | hNav1.7: Reduction in current at 20 mV (normalized data) Delta Ratio | hNav1.7: Voltage dependence of activation (mV) VDEP | hNav1.7: Voltage dependence of fast inactivation (mV) VDEP |
|---|---|---|---|---|
| 71 | −8.5 | −0.07 | −10.5 | −6.3 |
| 72 | −6.7 | −0.07 | −3.3 | −7.3 |
| 73 | −3.7 | −0.07 | −12.5 | −5.4 |
| 74 | −7.4 | −0.07 | −3.7 | −8.8 |
| 75 | −2.3 | −0.06 | −15.4 | −3.7 |
| 76 | −0.3 | −0.06 | −11.4 | −3.9 |
| 77 | −0.3 | −0.06 | −2.2 | −5 |
| 78 | −4.2 | −0.04 | −10.5 | −4.6 |
| 79 | −5.8 | −0.04 | −15.2 | −7.9 |
| 80 | −7.2 | −0.03 | −9.3 | −3.8 |
| 81 | −2.8 | −0.02 | −10.3 | −5 |
| 82 | −2.5 | −0.02 | −5.6 | −8.7 |
| 83 | −1.5 | 0.01 | −3.1 | −0.5 |
| 84 | 0 | 0.02 | −6.7 | −2.4 |
| 85 | 0.3 | 0.03 | −3.4 | −3.2 |
| 89 | −3.6 | −0.01 | −10.6 | −4.4 |
| 90 | 2.3 | 0.01 | −2.9 | 0.1 |
| 91 | −3.1 | 0.01 | −5 | −4.1 |
| 92 | −2.2 | 0.01 | −7.1 | −3.9 |

TABLE 3

| No. | Nav1.7 IC50 INWARD CURRENT BLOCK (nM) (7 Hz, Automated Patchclamp) | Nav1.7 IC50 P1 BLOCK (nM) (Automated Patchclamp) | Nav1.7 IC50 SLOW INACTIVATION BLOCK (nM) (Automated Patchclamp) | Nav1.7 IC50 INWARD CURRENT BLOCK (nM) (0.25 Hz, Automated Patchclamp) | Nav1.7 IC50 INWARD CURRENT BLOCK (nM) (7 Hz, Manual Patchclamp) | Nav1.7 IC50 SLOW INACTIVATION BLOCK (nM) (Manual Patchclamp) | Electrophysiological Characterization |
|---|---|---|---|---|---|---|---|
| 1 |  | 15500.00 | 2580.00 |  |  | 568.00 | STATE-DEPENDENT, BLOCKER OF SLOW INACTIVATION |
| 6 | 1660.00 | 12700.00 | 2770.00 |  |  |  |  |
| 10 | 1890.00 | 11500.00 | 4120.00 |  |  |  | STATE-DEPENDENT, BLOCKER OF SLOW INACTIVATION |
| 16 | 9620.00 | 15000.00 | 8120.00 | 15000.00 | 23200.00 | 3500.00 | STATE-DEPENDENT, BLOCKER OF SLOW INACTIVATION |
| 38 |  | 10300 | 5320 |  |  | 436 | STATE-DEPENDENT, BLOCKER OF SLOW INACTIVATION |
| 54 |  |  | 2890 |  |  | 312 | STATE-DEPENDENT, BLOCKER OF SLOW INACTIVATION |
| 75 | 15000 | 15000 | 15000 |  |  |  |  |

Example 3: Pain Test Assays

As discussed above, the compounds described herein can be tested for efficacy in any standard animal model of pain, wherein the animal's response to the application or injection of a chemical irritant to the skin, muscle joints, or internal organs is measured.

The formalin test in rats was performed as previously described (McNamara, 2007. *Proc. Natl. Acad. Sci.*, vol 104, page 13525) using an automated flinch-detecting system (T. Yaksh, University of California at San Diego, La Jolla, Calif.). On the day of testing, a small metal band (0.5 g) was loosely placed around the right hind paw of a male Sprague-Dawley rat (average weight, ~250 g). The rats were allowed to acclimate to a Plexiglas chamber for at least 30 min before testing. Formalin was then injected (50 μl of 2.5% formalin, diluted in saline) into the dorsal surface of the right hind paw of the rat, and the animal was put into a chamber of the automated formalin apparatus where movement of the formalin-injected paw was recorded. The number of paw flinches per minute was tallied for the next 60 minutes. The time interval phases were defined as follows: Phase I (0-9 mins), Phase II (10-60 mins), Phase IIA (10-40 mins), and Phase IIB (41-60 mins). The following compounds were administered 1 hour prior to formalin administration. Compound 52 from Table 1 was administered by oral gavage in 4% DMSO, 10% Solutol, 86% H$_2$O. Gabapentin was administered subcutaneously in 0.9% NaCl (aq). The results are shown in Table. 4.

TABLE 4

| Treatment | Phase 1 | Phase 2a | Phase 2b | Total Phase 2 |
| --- | --- | --- | --- | --- |
| Vehicle | 301 ± 91 | 966 ± 217 | 352 ± 202 | 1318 ± 352 |
| Compound 52 3 mg/kg | 345 ± 75 | 988 ± 139 | 377 ± 79 | 1365 ± 174 |
| Compound 52 10 mg/kg | 315 ± 58 | 758 ± 199* | 204 ± 66* | 962 ± 189* |
| Compound 52 30 mg/kg | 333 ± 75 | 706 ± 261** | 147 ± 101* | 853 ± 259* |
| Gabapentin 100 mg/kg SC | 320 ± 58 | 486 ± 202*** | 77 ± 47*** | 562 ± 213** |

*p < 0.05;
**p < 0.01;
***p < 0.001;
1-tailed t-test versus vehicle

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A compound of Formula X:

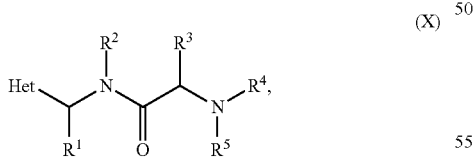
(X)

wherein Het is selected from the group consisting of

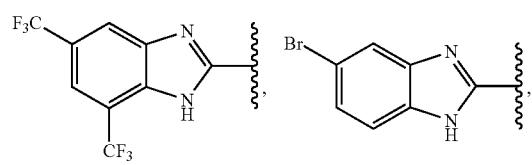

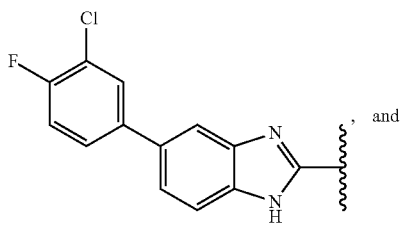
, and

-continued

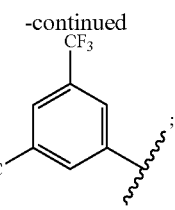
;

R$^1$ is H;

R$^2$ is H or optionally substituted C1 to C6 alkyl;

R$^3$ is H, optionally substituted C1-C6 alkyl, or optionally substituted phenyl;

R$^4$ is C1-C6 alkyl substituted with halo, CN, NO$_2$, CF$_3$, OCF$_3$, COOR', CONR'$_2$, OR', SR', SOR', SO$_2$R', NR'$_2$, NR'(CO)R', NR'C(O)OR', NR'C(O)NR'$_2$, NR'SO$_2$NR'$_2$, =NOR', =O or NR'SO$_2$R', wherein each R' is independently H or an optionally substituted group selected from alkyl, alkenyl, alkynyl, heteroalkyl, heteroalkenyl, heteroalkynyl, heteroaryl and aryl; and R$^5$ is H or an optionally substituted C1-C6 alkyl;

or a stereoisomer thereof, or a pharmaceutically acceptable salt thereof.

2. The compound of claim 1, wherein R$^5$ is H.

3. The stereoisomer of the compound of claim 1.

4. The pharmaceutically acceptable salt of the compound of claim 1.

5. A pharmaceutical composition comprising
   (1) the compound of claim 1, of a stereoisomer thereof, or a pharmaceutically acceptable salt thereof; and
   (2) a pharmaceutically acceptable carrier or excipient.

6. The pharmaceutical composition of claim 5, wherein said pharmaceutical composition is formulated in unit dosage form.

7. The pharmaceutical composition of claim 6, wherein said unit dosage form is a tablet, caplet, capsule, lozenge, film, strip, gelcap, or syrup.

8. A compound of Formula X:

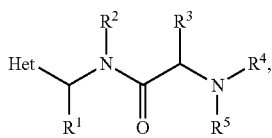

wherein Het is selected from the group consisting of

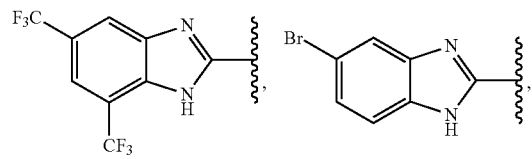

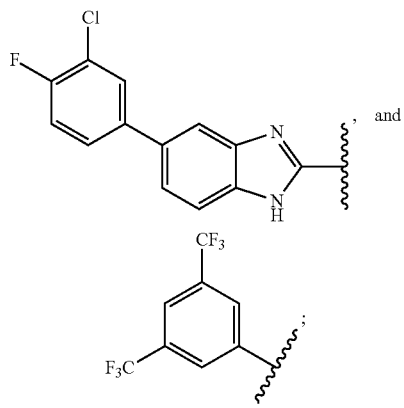

R¹ is H;
R² is H or optionally substituted C1 to C6 alkyl;
R³ is H, optionally substituted C1-C6 alkyl or optionally substituted phenyl;
R⁴ is —CO₂tBu, or —C(O)H; and
R⁵ is H or an optionally substituted C1-C6 alkyl;
or a stereoisomer thereof, or a pharmaceutically acceptable salt thereof.

9. The compound of claim 8, wherein R⁵ is H.

10. The stereoisomer of the compound of claim 8.

11. The pharmaceutically acceptable salt of the compound of claim 8.

12. A pharmaceutical composition comprising
(3) the compound of claim 8, of a stereoisomer thereof, or a pharmaceutically acceptable salt thereof; and
(4) a pharmaceutically acceptable carrier or excipient.

13. The pharmaceutical composition of claim 12, wherein said pharmaceutical composition is formulated in unit dosage form.

14. The pharmaceutical composition of claim 13, wherein said unit dosage form is a tablet, caplet, capsule, lozenge, film, strip, gelcap, or syrup.

15. A compound selected from the group consisting of:

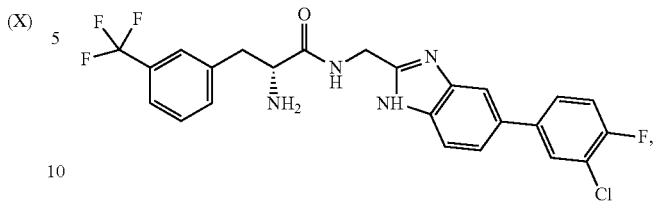

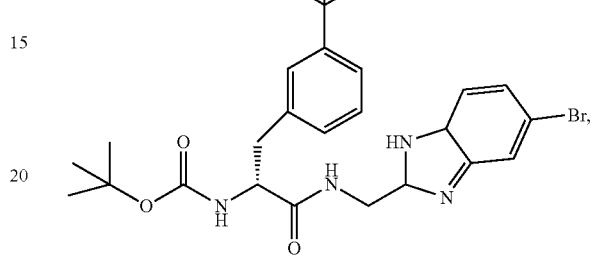

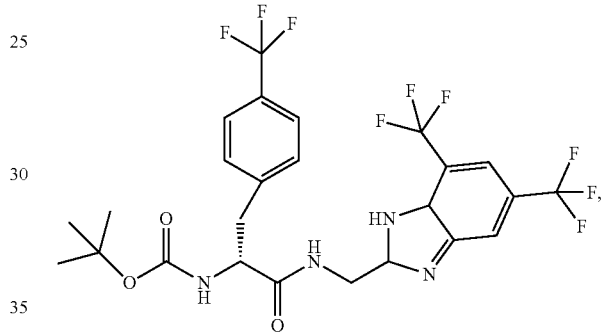

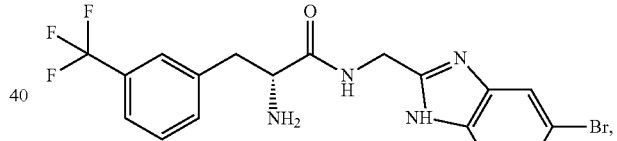

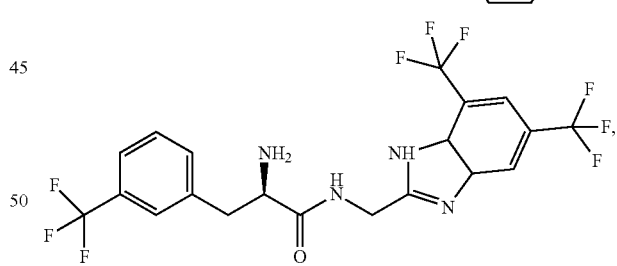

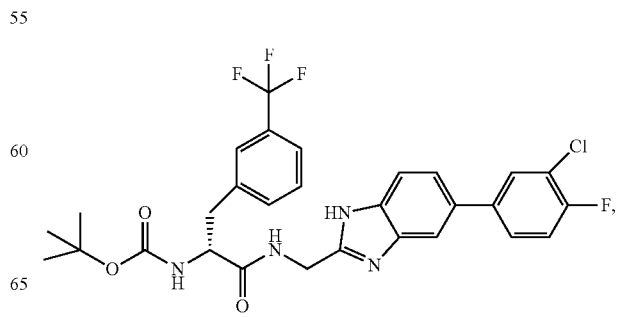

-continued
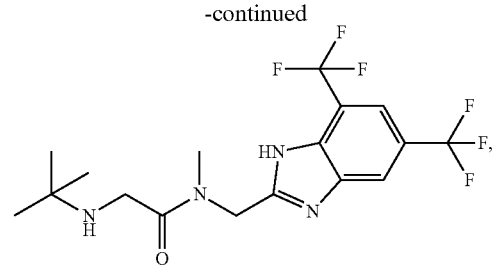
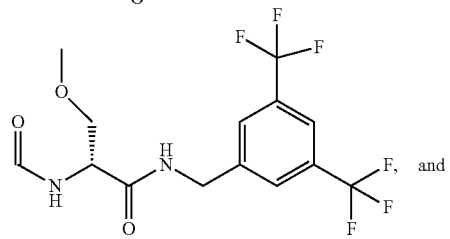
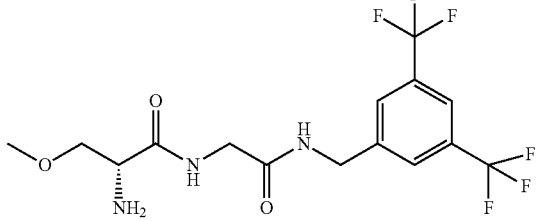
and stereoisomers thereof, and pharmaceutically acceptable salts thereof.
* * * * *